US011147637B2

(12) United States Patent
Romo et al.

(10) Patent No.: US 11,147,637 B2
(45) Date of Patent: Oct. 19, 2021

(54) LOW FRICTION INSTRUMENT DRIVER INTERFACE FOR ROBOTIC SYSTEMS

(71) Applicant: Auris Health, Inc., Redwood City, CA (US)

(72) Inventors: Enrique Romo, Dublin, CA (US); J. Scot Hart, Jr., Menlo Park, CA (US); Travis Covington, Sunnyvale, CA (US)

(73) Assignee: Auris Health, Inc., Redwood City, CA (US)

( * ) Notice: Subject to any disclaimer, the term of this patent is extended or adjusted under 35 U.S.C. 154(b) by 988 days.

(21) Appl. No.: 15/228,743

(22) Filed: Aug. 4, 2016

(65) Prior Publication Data

US 2016/0338783 A1 Nov. 24, 2016

Related U.S. Application Data

(63) Continuation of application No. 13/481,536, filed on May 25, 2012, now abandoned.

(51) Int. Cl.
*A61B 34/30* (2016.01)
*A61B 90/00* (2016.01)
(Continued)

(52) U.S. Cl.
CPC .............. *A61B 34/30* (2016.02); *A61B 90/06* (2016.02); *A61B 17/00* (2013.01);
(Continued)

(58) Field of Classification Search
CPC ........ A61B 19/2203; A61B 2019/2223; A61B 2017/00477; A61B 34/30;
(Continued)

(56) References Cited

U.S. PATENT DOCUMENTS 2,556,601 A 6/1951 Schofield
2,566,183 A 8/1951 Forss
(Continued)

FOREIGN PATENT DOCUMENTS

CN 101500470 8/2009
CN 103037799 4/2011
(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

*Primary Examiner* — Wade Miles
*Assistant Examiner* — Michael G Mendoza
(74) *Attorney, Agent, or Firm* — Frost Brown Todd LLC

(57) ABSTRACT

A medical robotic system includes a base having a first opening, and a first protrusion next to the first opening, a first rotary member configured for detachably coupling to a component of the medical robotic system in a manner such that the first rotary member is rotatable relative to the base and at least a part of the first rotary member is located in the first opening of the base when the first rotary member is coupled to the system component, and a cover coupled to the base, wherein the first rotary member comprises a first end, a second end, a body extending between the first and second ends, and a flange disposed circumferentially around a part of the body, the flange having a first circumferential slot for receiving the first protrusion.

17 Claims, 26 Drawing Sheets

2 5 10 16 3 14 39 22 20 13 9

(51) Int. Cl.
*A61B 18/14* (2006.01)
*A61B 17/00* (2006.01)
*A61B 18/00* (2006.01)

(52) U.S. Cl.
CPC . *A61B 18/1492* (2013.01); *A61B 2017/00477* (2013.01); *A61B 2018/00029* (2013.01); *A61B 2034/301* (2016.02); *A61B 2090/064* (2016.02); *A61B 2090/066* (2016.02)

(58) Field of Classification Search
CPC ... A61B 2034/304; A61B 90/00; A61B 50/00; A61B 46/10; A61B 90/06; A61B 2090/066; A61B 2034/301; A61B 18/1492; A61M 39/18
See application file for complete search history.

(56) References Cited

U.S. PATENT DOCUMENTS 2,623,175 A 12/1952 Finke
2,730,699 A 1/1956 Gratian
2,884,808 A 5/1959 Mueller
3,294,183 A 12/1966 Riley et al.
3,472,083 A 10/1969 Schnepel
3,513,724 A 5/1970 Box
3,595,074 A 7/1971 Johnson
3,734,207 A 5/1973 Fishbein
3,739,923 A 6/1973 Totsuka
3,784,031 A 1/1974 Nitu
3,790,002 A 2/1974 Guilbaud et al.
3,921,536 A 11/1975 Savage
3,926,386 A 12/1975 Stahmann
4,141,245 A 2/1979 Brandstetter
4,241,884 A 12/1980 Lynch
4,243,034 A 1/1981 Brandt
4,351,493 A 9/1982 Sonnek
4,357,843 A 11/1982 Peck et al.
4,384,493 A 5/1983 Grunbaum
4,507,026 A 3/1985 Lund
4,530,471 A 7/1985 Inoue
4,555,960 A 12/1985 King
4,688,555 A 8/1987 Wardle
4,745,908 A 5/1988 Wardle
4,784,150 A 11/1988 Voorhies et al.
4,857,058 A 8/1989 Payton
4,907,168 A 3/1990 Boggs
4,945,790 A 8/1990 Golden
5,207,128 A 5/1993 Albright
5,234,428 A 8/1993 Kaufman
5,256,150 A 10/1993 Quiachon et al.
5,277,085 A 1/1994 Tanimura et al.
5,350,101 A 9/1994 Godlewski
5,426,687 A 6/1995 Goodall et al.
5,507,725 A 4/1996 Savage et al.
5,524,180 A 6/1996 Wang et al.
5,559,294 A 9/1996 Hoium et al.
5,709,661 A 1/1998 Van Egmond
5,767,840 A 6/1998 Selker
5,779,623 A 7/1998 Bonnell
5,792,135 A 8/1998 Madhani et al.
5,797,900 A 8/1998 Madhani
5,855,583 A 1/1999 Wang et al.
5,921,968 A 7/1999 Lampropoulos et al.
5,967,934 A 10/1999 Ishida et al.
6,077,219 A 6/2000 Viebach
6,084,371 A 7/2000 Kress et al.
6,154,000 A 11/2000 Rastegar et al.
6,171,234 B1 1/2001 White et al.
6,185,478 B1 2/2001 Koakutsu et al.
6,272,371 B1 8/2001 Shlomo
6,289,579 B1 9/2001 Viza et al.
6,394,998 B1 5/2002 Wallace et al.
6,401,572 B1 6/2002 Provost
6,436,107 B1 8/2002 Wang et al.
6,487,940 B2 12/2002 Hart et al.
6,491,701 B2 12/2002 Tierney et al.
6,695,818 B2 2/2004 Wollschlager
6,726,675 B1 4/2004 Beyar
6,786,896 B1 9/2004 Madhani et al.
6,827,712 B2 12/2004 Tovey et al.
7,044,936 B2 5/2006 Harding
7,172,580 B2 2/2007 Hruska et al.
7,276,044 B2 10/2007 Ferry et al.
7,615,042 B2 11/2009 Beyar et al.
7,635,342 B2 12/2009 Ferry et al.
7,666,191 B2 2/2010 Orban, III et al.
7,766,856 B2 8/2010 Ferry et al.
7,850,642 B2 12/2010 Moll et al.
7,938,809 B2 5/2011 Lampropoulos et al.
7,974,674 B2 7/2011 Hauck et al.
7,998,020 B2 8/2011 Kidd et al.
8,050,523 B2 11/2011 Younge et al.
8,052,621 B2 11/2011 Wallace et al.
8,052,636 B2 11/2011 Moll et al.
8,092,397 B2 1/2012 Wallace et al.
8,157,308 B2 4/2012 Pedersen
8,182,415 B2 5/2012 Larkin et al.
8,277,417 B2 10/2012 Fedinec et al.
8,291,791 B2 10/2012 Light et al.
8,414,505 B1 4/2013 Weitzner
8,425,465 B2 4/2013 Nagano
8,602,031 B2 12/2013 Reis et al.
8,671,817 B1 3/2014 Bogusky
8,720,448 B2 5/2014 Reis et al.
8,746,252 B2 6/2014 McGrogan et al.
8,827,948 B2 9/2014 Romo et al.
8,870,815 B2 10/2014 Bhat et al.
8,894,610 B2 11/2014 MacNamara et al.
8,961,533 B2 2/2015 Stahler et al.
8,968,333 B2 3/2015 Yu et al.
8,992,542 B2 3/2015 Hagag et al.
9,173,713 B2 11/2015 Hart et al.
9,204,933 B2 12/2015 Reis et al.
9,254,123 B2 2/2016 Alvarez et al.
9,326,822 B2 5/2016 Lewis et al.
9,408,669 B2 8/2016 Kokish et al.
9,446,177 B2 9/2016 Millman et al.
9,452,018 B2 9/2016 Yu
9,457,168 B2 10/2016 Moll et al.
9,498,601 B2 11/2016 Tanner et al.
9,504,604 B2 11/2016 Alvarez
9,561,083 B2 2/2017 Yu et al.
9,622,827 B2 4/2017 Yu et al.
9,636,184 B2 5/2017 Lee et al.
9,636,483 B2 5/2017 Hart et al.
9,668,814 B2 6/2017 Kokish
9,713,509 B2 7/2017 Schuh et al.
9,727,963 B2 8/2017 Mintz et al.
9,737,371 B2 8/2017 Romo et al.
9,737,373 B2 8/2017 Schuh
9,744,335 B2 8/2017 Jiang
9,763,741 B2 9/2017 Alvarez et al.
9,788,910 B2 10/2017 Schuh
9,818,681 B2 11/2017 Machida
9,844,412 B2 12/2017 Bogusky et al.
9,867,635 B2 1/2018 Alvarez et al.
9,918,681 B2 3/2018 Wallace et al.
9,931,025 B1 4/2018 Graetzel et al.
9,949,749 B2 4/2018 Noonan et al.
9,955,986 B2 5/2018 Shah
9,962,228 B2 5/2018 Schuh et al.
9,980,785 B2 5/2018 Schuh
9,993,313 B2 6/2018 Schuh et al.
10,016,900 B1 7/2018 Meyer et al.
10,022,192 B1 7/2018 Ummalaneni
10,143,360 B2 12/2018 Roelle et al.
10,145,747 B1 12/2018 Lin et al.
10,159,532 B1 12/2018 Ummalaneni et al.
10,524,866 B2 1/2020 Srinivasan
10,639,114 B2 5/2020 Schuh
10,667,875 B2 6/2020 DeFonzo
2001/0042643 A1 11/2001 Krueger et al.
2002/0045905 A1 4/2002 Gerbi et al.

(56) References Cited

U.S. PATENT DOCUMENTS

2002/0098938 A1 7/2002 Milbourne et al.
2002/0100254 A1 8/2002 Dharssi
2002/0107573 A1 8/2002 Steinberg
2002/0117017 A1 8/2002 Bernhardt et al.
2002/0161355 A1 10/2002 Wollschlager
2002/0161426 A1 10/2002 Lancea
2002/0177789 A1 11/2002 Ferry et al.
2003/0056561 A1 3/2003 Butscher et al.
2003/0212308 A1 11/2003 Bendall
2004/0015053 A1 1/2004 Bieger
2004/0152972 A1 8/2004 Hunter
2004/0243147 A1 12/2004 Lipow
2004/0254566 A1 12/2004 Plicchi
2005/0004579 A1 1/2005 Schneider et al.
2005/0177026 A1 8/2005 Hoeg et al.
2005/0183532 A1 8/2005 Najaf et al.
2005/0222554 A1 10/2005 Wallace et al.
2006/0041245 A1 2/2006 Ferry
2006/0095022 A1 5/2006 Moll et al.
2006/0100610 A1 5/2006 Wallace et al.
2006/0111692 A1 5/2006 Hlavka et al.
2006/0146010 A1 7/2006 Schneider
2006/0201688 A1 9/2006 Jenner et al.
2006/0229587 A1 10/2006 Beyar et al.
2006/0237205 A1 10/2006 Sia et al.
2007/0000498 A1 1/2007 Glynn et al.
2007/0013336 A1 1/2007 Nowlin et al.
2007/0060879 A1 3/2007 Weitzner et al.
2007/0100201 A1 5/2007 Komiya et al.
2007/0100254 A1 5/2007 Murakami
2007/0112355 A1 5/2007 Salahieh
2007/0119274 A1 5/2007 Devengenzo et al.
2007/0149946 A1 6/2007 Viswanathan
2007/0156123 A1 7/2007 Moll et al.
2007/0191177 A1 8/2007 Nagai et al.
2007/0233044 A1 10/2007 Wallace et al.
2007/0239028 A1 10/2007 Houser
2007/0245175 A1 10/2007 Zheng et al.
2007/0265503 A1 11/2007 Schlesinger et al.
2007/0299427 A1 12/2007 Yeung et al.
2008/0039255 A1 2/2008 Jinno et al.
2008/0046122 A1 2/2008 Manzo et al.
2008/0065103 A1 3/2008 Cooper et al.
2008/0140087 A1 6/2008 Barbagli
2008/0147011 A1 6/2008 Urmey
2008/0177285 A1 7/2008 Brock et al.
2008/0214925 A1 9/2008 Wilson et al.
2008/0218770 A1 9/2008 Moll et al.
2008/0243064 A1 10/2008 Stahler et al.
2008/0249536 A1 10/2008 Stahler et al.
2008/0253108 A1 10/2008 Yu et al.
2008/0255505 A1 10/2008 Carlson et al.
2008/0262301 A1 10/2008 Gibbons et al.
2008/0285909 A1 11/2008 Younge et al.
2008/0287963 A1 11/2008 Rogers et al.
2008/0302200 A1 12/2008 Tobey
2009/0082722 A1 3/2009 Munger et al.
2009/0098971 A1 4/2009 Ho et al.
2009/0105645 A1 4/2009 Kidd et al.
2009/0123111 A1 5/2009 Udd
2009/0137952 A1 5/2009 Ramamurthy et al.
2009/0163948 A1 6/2009 Sunaoshi
2009/0171371 A1 7/2009 Nixon
2009/0247944 A1 10/2009 Kirschenman et al.
2009/0248039 A1 10/2009 Cooper et al.
2010/0016852 A1 1/2010 Manzo et al.
2010/0030023 A1 2/2010 Yoshie
2010/0069833 A1 3/2010 Wenderow et al.
2010/0073150 A1 3/2010 Olson et al.
2010/0114115 A1 5/2010 Schlesinger et al.
2010/0130923 A1 5/2010 Cleary et al.
2010/0130987 A1 5/2010 Wenderow et al.
2010/0170519 A1* 7/2010 Romo .................... A61B 34/30 128/852
2010/0175701 A1 7/2010 Reis et al.
2010/0204646 A1 8/2010 Plicchi et al.
2010/0210923 A1 8/2010 Li et al.
2010/0228191 A1 9/2010 Alvarez et al.
2010/0248177 A1 9/2010 Mangelberger et al.
2010/0249506 A1 9/2010 Prisco et al.
2010/0274078 A1 10/2010 Kim et al.
2010/0331856 A1 12/2010 Carlson et al.
2011/0015484 A1 1/2011 Alvarez et al.
2011/0015648 A1 1/2011 Alvarez et al.
2011/0015650 A1 1/2011 Choi et al.
2011/0028991 A1 2/2011 Ikeda et al.
2011/0090486 A1 4/2011 Udd
2011/0130718 A1 6/2011 Kidd et al.
2011/0147030 A1 6/2011 Blum et al.
2011/0152880 A1 6/2011 Alvarez et al.
2011/0238083 A1 9/2011 Moll et al.
2011/0261183 A1 10/2011 Ma et al.
2011/0277775 A1 11/2011 Holop et al.
2011/0288573 A1 11/2011 Yates et al.
2011/0295268 A1 12/2011 Roelle et al.
2011/0306836 A1 12/2011 Ohline et al.
2011/0319714 A1 12/2011 Roelle et al.
2011/0319815 A1 12/2011 Roelle et al.
2011/0319910 A1 12/2011 Roelle et al.
2012/0071821 A1 3/2012 Yu
2012/0071822 A1 3/2012 Romo et al.
2012/0071894 A1 3/2012 Tanner et al.
2012/0071895 A1 3/2012 Stahler et al.
2012/0143226 A1 6/2012 Belson et al.
2012/0150154 A1 6/2012 Brisson et al.
2012/0186194 A1 7/2012 Schlieper
2012/0191107 A1 7/2012 Tanner et al.
2012/0232476 A1 9/2012 Bhat et al.
2012/0239012 A1 9/2012 Laurent et al.
2012/0277730 A1 11/2012 Salahieh
2012/0283747 A1 11/2012 Popovic
2013/0018400 A1 1/2013 Milton et al.
2013/0144116 A1 6/2013 Cooper et al.
2013/0231678 A1 9/2013 Wenderow
2013/0304084 A1 11/2013 Beira et al.
2013/0317519 A1 11/2013 Romo et al.
2013/0345519 A1 12/2013 Piskun et al.
2014/0000411 A1 1/2014 Shelton, IV et al.
2014/0066944 A1 3/2014 Taylor et al.
2014/0069437 A1 3/2014 Reis et al.
2014/0142591 A1 5/2014 Alvarez et al.
2014/0166023 A1 6/2014 Kishi
2014/0171778 A1 6/2014 Tsusaka
2014/0180063 A1 6/2014 Zhao
2014/0222019 A1 8/2014 Brudnick
2014/0243849 A1 8/2014 Saglam et al.
2014/0276233 A1 9/2014 Murphy
2014/0276389 A1 9/2014 Walker
2014/0276394 A1 9/2014 Wong et al.
2014/0276594 A1 9/2014 Tanner et al.
2014/0276935 A1 9/2014 Yu
2014/0276936 A1 9/2014 Kokish et al.
2014/0277334 A1 9/2014 Yu et al.
2014/0309649 A1 10/2014 Alvarez et al.
2014/0357984 A1 12/2014 Wallace et al.
2014/0364870 A1 12/2014 Alvarez et al.
2014/0375784 A1 12/2014 Massetti
2014/0379000 A1 12/2014 Romo et al.
2015/0012134 A1 1/2015 Robinson
2015/0051592 A1 2/2015 Kintz
2015/0090063 A1 4/2015 Lantermann et al.
2015/0101442 A1 4/2015 Romo
2015/0119638 A1 4/2015 Yu et al.
2015/0133963 A1 5/2015 Barbagli
2015/0142013 A1 5/2015 Tanner et al.
2015/0144514 A1 5/2015 Brennan et al.
2015/0148600 A1 5/2015 Ashinuma et al.
2015/0150635 A1 6/2015 Kilroy
2015/0164594 A1 6/2015 Romo et al.
2015/0164596 A1 6/2015 Romo
2015/0182250 A1 7/2015 Conlon et al.
2015/0231364 A1 8/2015 Blanchard
2015/0297864 A1 10/2015 Kokish et al.
2015/0327939 A1 11/2015 Kokish et al.

(56) References Cited

U.S. PATENT DOCUMENTS

2015/0335480 A1 11/2015 Alvarez et al.
2015/0374445 A1 12/2015 Gombert et al.
2016/0000512 A1 1/2016 Gombert et al.
2016/0001038 A1 1/2016 Romo et al.
2016/0151122 A1 6/2016 Alvarez et al.
2016/0157945 A1 6/2016 Madhani
2016/0166234 A1 6/2016 Zhang
2016/0192860 A1 7/2016 Allenby
2016/0206389 A1 7/2016 Miller
2016/0213435 A1 7/2016 Hourtash
2016/0235946 A1 8/2016 Lewis et al.
2016/0270865 A1 9/2016 Landey et al.
2016/0287279 A1 10/2016 Bovay et al.
2016/0296294 A1 10/2016 Moll et al.
2016/0338783 A1 11/2016 Romo et al.
2016/0338785 A1 11/2016 Kokish et al.
2016/0346049 A1 12/2016 Allen et al.
2016/0354582 A1 12/2016 Yu et al.
2016/0374541 A1 12/2016 Agrawal et al.
2017/0007337 A1 1/2017 Dan
2017/0007343 A1 1/2017 Yu
2017/0071684 A1 3/2017 Kokish et al.
2017/0100199 A1 4/2017 Yu et al.
2017/0105804 A1 4/2017 Yu
2017/0119413 A1 5/2017 Romo
2017/0119481 A1 5/2017 Romo et al.
2017/0119484 A1 5/2017 Tanner et al.
2017/0151028 A1 6/2017 Ogawa et al.
2017/0165011 A1 6/2017 Bovay et al.
2017/0172673 A1 6/2017 Yu et al.
2017/0202627 A1 7/2017 Sramek et al.
2017/0209073 A1 7/2017 Sramek et al.
2017/0209672 A1 7/2017 Hart et al.
2017/0252540 A1 9/2017 Weitzner et al.
2017/0258534 A1 9/2017 Hourtash
2017/0281049 A1 10/2017 Yamamoto
2017/0290631 A1 10/2017 Lee et al.
2017/0296784 A1 10/2017 Kokish
2017/0312481 A1 11/2017 Covington et al.
2017/0333679 A1 11/2017 Jiang
2017/0340396 A1 11/2017 Romo et al.
2017/0365055 A1 12/2017 Mintz et al.
2017/0367782 A1 12/2017 Schuh et al.
2018/0025666 A1 1/2018 Ho et al.
2018/0042464 A1 2/2018 Arai
2018/0049792 A1 2/2018 Eckert
2018/0056044 A1 3/2018 Choi et al.
2018/0104820 A1 4/2018 Troy et al.
2018/0116735 A1 5/2018 Tierney et al.
2018/0177383 A1 6/2018 Noonan et al.
2018/0177556 A1 6/2018 Noonan et al.
2018/0177561 A1 6/2018 Mintz et al.
2018/0206927 A1 7/2018 Prisco et al.
2018/0214011 A1 8/2018 Graetzel et al.
2018/0221038 A1 8/2018 Noonan et al.
2018/0221039 A1 8/2018 Shah
2018/0250083 A1 9/2018 Schuh et al.
2018/0271616 A1 9/2018 Schuh et al.
2018/0279852 A1 10/2018 Rafii-Tari et al.
2018/0280660 A1 10/2018 Landey et al.
2018/0289243 A1 10/2018 Landey et al.
2018/0289431 A1 10/2018 Draper et al.
2018/0296299 A1 10/2018 Iceman
2018/0303566 A1 10/2018 Soundararajan
2018/0325499 A1 11/2018 Landey et al.
2018/0326181 A1 11/2018 Kokish et al.
2018/0333044 A1 11/2018 Jenkins
2018/0360435 A1 12/2018 Romo
2019/0000559 A1 1/2019 Berman et al.
2019/0000560 A1 1/2019 Berman et al.
2019/0000566 A1 1/2019 Graetzel et al.
2019/0000568 A1 1/2019 Connolly et al.
2019/0000576 A1 1/2019 Mintz et al.
2019/0083183 A1 3/2019 Moll et al.
2019/0105776 A1 4/2019 Ho et al.
2019/0105785 A1 4/2019 Meyer
2019/0107454 A1 4/2019 Lin
2019/0110839 A1 4/2019 Rafii-Tari et al.
2019/0110843 A1 4/2019 Ummalaneni et al.
2019/0151148 A1 4/2019 Alvarez et al.
2019/0228528 A1 4/2019 Mintz et al.
2019/0142537 A1 5/2019 Covington et al.
2019/0167366 A1 6/2019 Ummalaneni
2019/0175009 A1 6/2019 Mintz
2019/0175062 A1 6/2019 Rafii-Tari et al.
2019/0175287 A1 6/2019 Hill
2019/0175799 A1 6/2019 Hsu
2019/0183585 A1 6/2019 Rafii-Tari et al.
2019/0183587 A1 6/2019 Rafii-Tari et al.
2019/0216548 A1 7/2019 Ummalaneni
2019/0216550 A1 7/2019 Eyre
2019/0216576 A1 7/2019 Eyre
2019/0223974 A1 7/2019 Romo
2019/0228525 A1 7/2019 Mintz et al.
2019/0246882 A1 8/2019 Graetzel et al.
2019/0262086 A1 8/2019 Connolly et al.
2019/0269468 A1 9/2019 Hsu et al.
2019/0274764 A1 9/2019 Romo
2019/0290109 A1 9/2019 Agrawal et al.
2019/0298160 A1 10/2019 Ummalaneni et al.
2019/0298460 A1 10/2019 Al-Jadda
2019/0298465 A1 10/2019 Chin
2019/0328213 A1 10/2019 Landey et al.
2019/0336238 A1 11/2019 Yu
2019/0365209 A1 12/2019 Ye et al.
2019/0365479 A1 12/2019 Rafii-Tari
2019/0365486 A1 12/2019 Srinivasan et al.
2019/0374297 A1 12/2019 Wallace et al.
2019/0375383 A1 12/2019 Alvarez
2019/0380787 A1 12/2019 Ye
2019/0380797 A1 12/2019 Yu
2020/0000533 A1 1/2020 Schuh
2020/0022767 A1 1/2020 Hill
2020/0039086 A1 2/2020 Meyer
2020/0046434 A1 2/2020 Graetzel
2020/0054408 A1 2/2020 Schuh et al.
2020/0060516 A1 2/2020 Baez
2020/0086087 A1 3/2020 Hart et al.
2020/0091799 A1 3/2020 Covington et al.
2020/0093549 A1 3/2020 Chin
2020/0093554 A1 3/2020 Schuh
2020/0100845 A1 4/2020 Julian
2020/0100853 A1 4/2020 Ho
2020/0100855 A1 4/2020 Leparmentier
2020/0101264 A1 4/2020 Jiang
2020/0107894 A1 4/2020 Wallace
2020/0121502 A1 4/2020 Kintz
2020/0129252 A1 4/2020 Kokish
2020/0146769 A1 5/2020 Eyre
2020/0155245 A1 5/2020 Yu
2020/0155801 A1 5/2020 Kokish
2020/0188043 A1 6/2020 Yu

FOREIGN PATENT DOCUMENTS

CN 102316817 1/2012
CN 102458295 5/2012
CN 102665590 9/2012
CN 102973317 3/2013
CN 102015759 4/2013
CN 103735313 4/2014
CN 105559850 5/2016
CN 105559886 5/2016
DE 19649082 1/1998
DE 102004020465 9/2005
EP 1 442 720 8/2004
EP 2 567 670 3/2013
EP 3 025 630 6/2016
JP 07-136173 5/1995
JP 2009-139187 6/2009
JP 2010-046384 3/2010
WO WO 02/074178 9/2002
WO WO 07/146987 12/2007
WO WO 09/092059 7/2009

(56) References Cited

FOREIGN PATENT DOCUMENTS

| | | |
|---|---|---|
| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/059412 | 4/2017 |
| WO | WO 17/0151993 | 9/2017 |

* cited by examiner

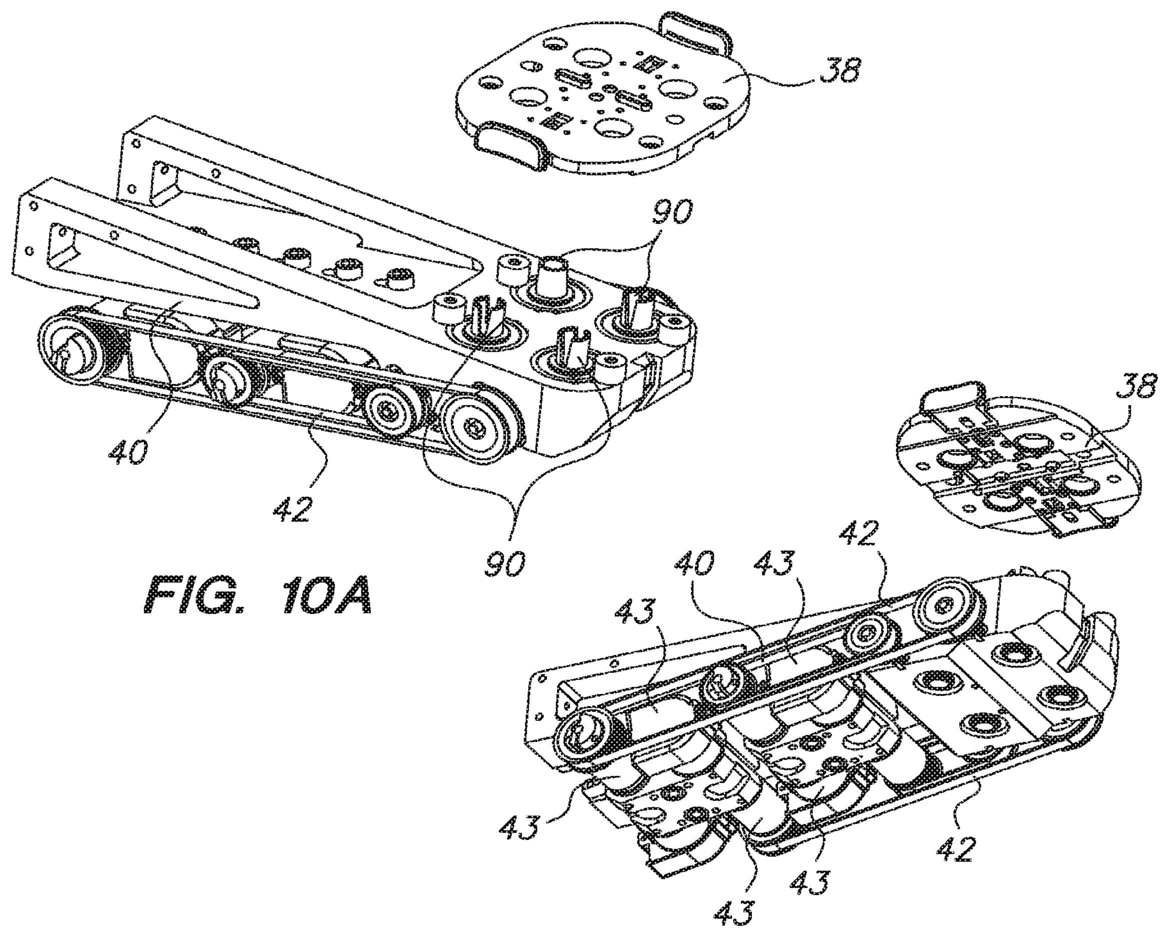
FIG. 10A
FIG. 10B
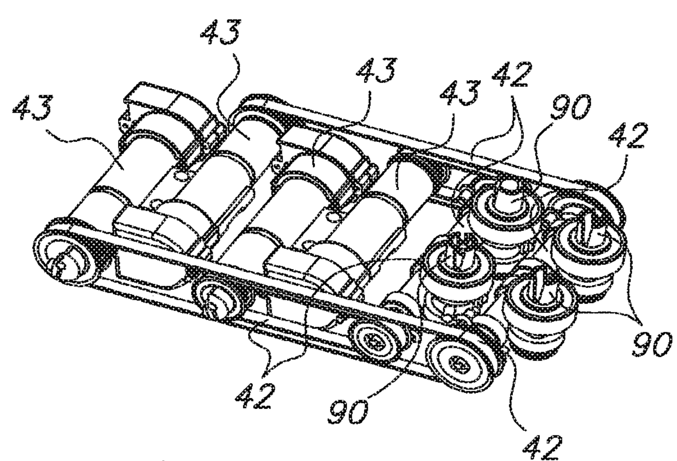
FIG. 10C

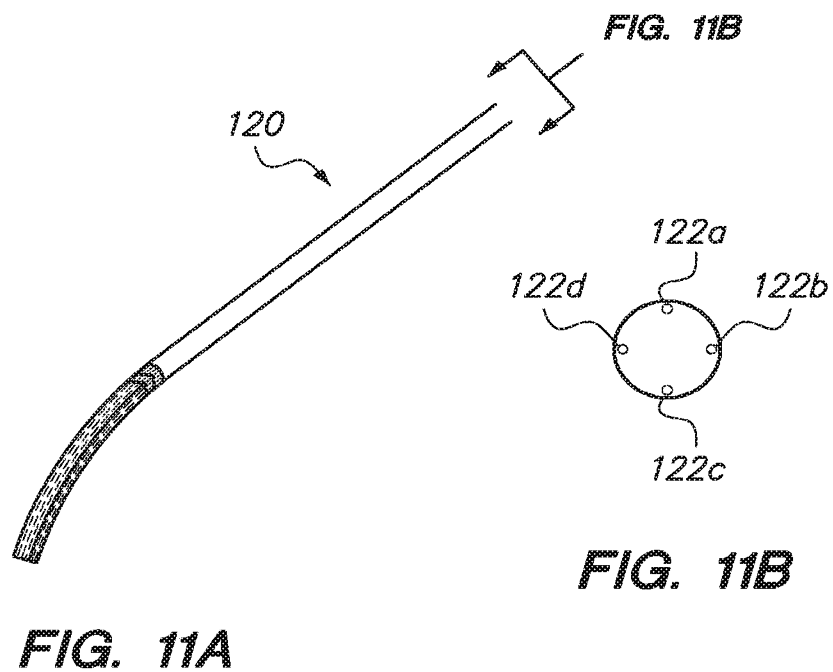
FIG. 11B
FIG. 11A
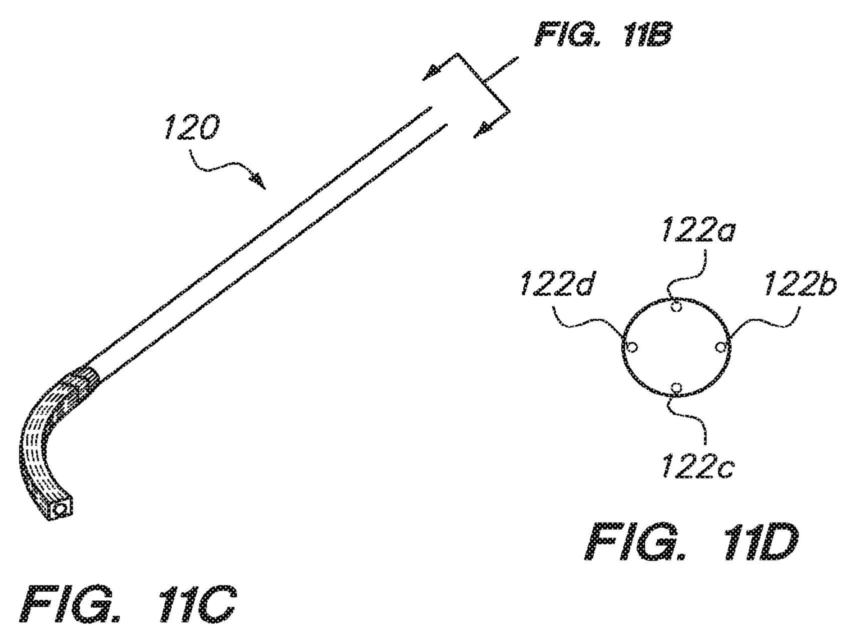
FIG. 11D
FIG. 11C

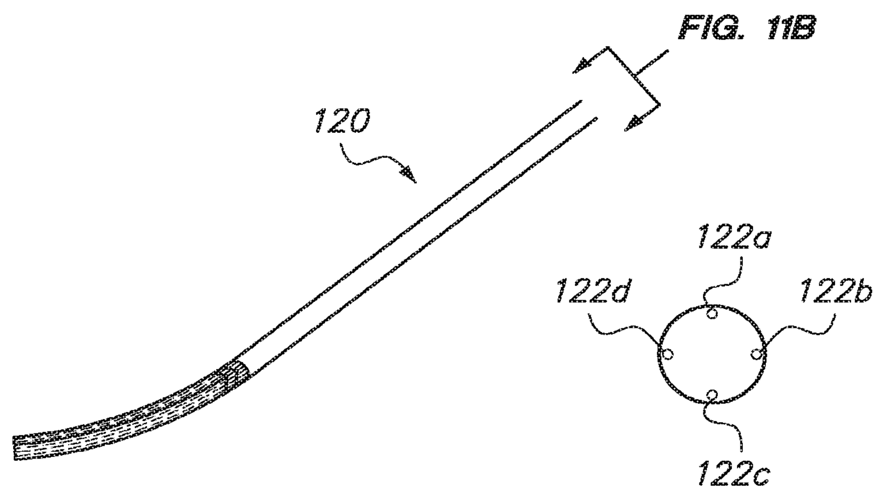
FIG. 11E
FIG. 11F
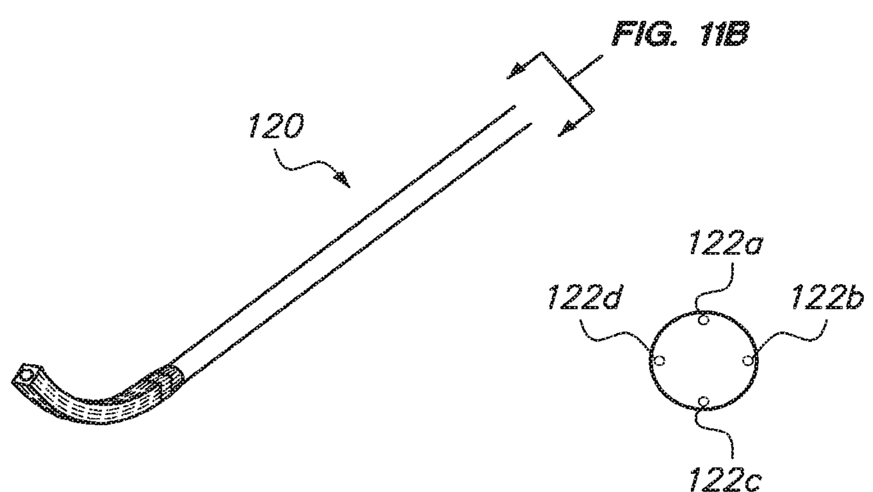
FIG. 11G
FIG. 11H

LOW FRICTION INSTRUMENT DRIVER INTERFACE FOR ROBOTIC SYSTEMS

CROSS-REFERENCE TO RELATED APPLICATION

This application is a continuation of U.S. patent application Ser. No. 13/481,536, filed May 25, 2012, now abandoned, and entitled "LOW FRICTION INSTRUMENT DRIVER INTERFACE FOR ROBOTIC SYSTEMS," the entirety of which is herein incorporated by reference for all purposes.

INCORPORATION BY REFERENCE

All of the following U.S. patent applications are expressly incorporated by reference herein for all purposes:

U.S. patent application Ser. No. 13/173,994, filed on Jun. 30, 2011, issued as U.S. Pat. No. 8,827,948 on Sep. 9, 2014, U.S. patent application Ser. No. 11/179,007, filed on Jul. 6, 2005, issued as U.S. Pat. No. 7,580,642 on Dec. 14, 2010, U.S. patent application Ser. No. 12/079,500, filed on Mar. 26, 2008, issued as U.S. Pat. No. 8,391,957 on Mar. 5, 2013, U.S. patent application Ser. No. 11/678,001, filed on Feb. 22, 2007, issued as U.S. Pat. No. 8,092,397 on Jan. 10, 2012, U.S. Patent Application No. 60/801,355, filed on May 17, 2006, U.S. patent application Ser. No. 11/804,585, filed on May 17, 2007, now abandoned U.S. patent application Ser. No. 11/640,099, filed on Dec. 14, 2006, issued as U.S. Pat. No. 8,498,691 on Jul. 30, 2013, U.S. patent application Ser. No. 12/507,727, filed on Jul. 22, 2009, now abandoned, U.S. patent application Ser. No. 12/106,254, filed on Apr. 18, 2008, issued as U.S. Pat. No. 8,050,523 on Nov. 1, 2011, U.S. patent application Ser. No. 12/192,033, filed on Aug. 14, 2008, issued as U.S. Pat. No. 9,186,046 on Nov. 17, 2015, U.S. patent application Ser. No. 12/236,478, filed on Sep. 23, 2008, issued as U.S. Pat. No. 8,989,528 on Mar. 24, 2015, U.S. patent application Ser. No. 12/833,935, filed on Jul. 9, 2010, now abandoned U.S. patent application Ser. No. 12/822,876, filed on Jun. 24, 2010, issued as U.S. Pat. No. 8,460,236 on Jun. 11, 2013, U.S. patent application Ser. No. 12/614,349, filed on Nov. 6, 2009, issued as U.S. Pat. No. 8,720,448 on May 13, 2014, U.S. patent application Ser. No. 11/690,116, filed Mar. 22, 2007, now abandoned, U.S. patent application Ser. No. 11/176,598, filed Jul. 6, 2005, now abandoned, U.S. patent application Ser. No. 12/012,795, filed Feb. 1, 2008, now abandoned, U.S. patent application Ser. No. 12/837,440, Jul. 15, 2010, issued as U.S. Pat. No. 8,780,339 on Jul. 15, 2014, U.S. Patent Application No. 61/513,488, filed Jul. 8, 2011, and U.S. patent application Ser. No. 13/174,605, filed Jun. 30, 2011, issued as U.S. Pat. No. 9,314,306 on Apr. 19, 2016.

FIELD

The application relates generally to robotically controlled surgical systems, and more particularly to flexible instruments and instrument drivers that are responsive to a master controller for performing surgical procedures to treat tissue, such as tissue in the livers.

BACKGROUND

Robotic surgical systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be preferably accessed only via naturally-occurring pathways such as blood vessels or the gastrointestinal tract.

In some cases, a robotic surgical system may include a steerable catheter with a steering wire, and an instrument driver for applying tension to the steering wire to steer the catheter. Applicant of the subject application determines that it would be desirable to sense a characteristic that corresponds with an amount of force or torque being applied to pull a steering wire of a robotic surgical system.

SUMMARY

In accordance with some embodiments, a medical robotic system includes a base having a first opening, and a first protrusion next to the first opening, a first rotary member configured for detachably coupling to a component of the medical robotic system in a manner such that the first rotary member is rotatable relative to the base and at least a part of the first rotary member is located in the first opening of the base when the first rotary member is coupled to the system component, and a cover coupled to the base, wherein the first rotary member comprises a first end, a second end, a body extending between the first and second ends, and a flange disposed circumferentially around a part of the body, the flange having a first circumferential slot for receiving the first protrusion.

In accordance with other embodiments, a medical robotic system includes an instrument driver having an actuatable element, a sensor coupled to the instrument driver, and a device configured for detachably coupling to the instrument driver, the device comprising a base having a first opening, and a rotary member configured for detachably coupling to the actuatable element of the instrument driver, wherein the rotary member is rotatable relative to the base, and at least a portion of the rotary member is located within the first opening of the base, wherein when the device is coupled to the instrument driver, the actuatable element is configured to rotate the rotary member in response to a command signal received from a user interface, and wherein the sensor is configured to sense a characteristic that corresponds with an amount of force or torque being applied to the actuatable element in order to rotate the rotary member.

In accordance with other embodiments, a method of steering a distal end of an elongate member includes determining a desired bending to be achieved by the distal end of the elongate member, determining an amount of tension to be applied to a steering wire located within the elongate member based on the desired bending to be achieved, using an actuatable element to apply a torque to turn a rotary member that is detachably coupled to the actuatable element, the steering wire having one end is secured to the rotary member and another end secured to the elongate member, wherein the application of the torque by the actuatable element causes tension to be applied to the steering wire, and using a sensor coupled to the actuatable element to sense a characteristic that corresponds with an amount of force or torque being applied by the actuatable element to turn the rotary member.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIGS. 10A and 10B illustrate different perspective views of the sheath block with sheath output plate positioned over receptacle sleeves.

FIG. 10C illustrates sheath articulation motors coupled to motor driven interfaces and receptacle sleeves.

FIGS. 11A-11H illustrate side and cross-sectional views of a catheter bent in various configurations with pull wire manipulation.

DESCRIPTION OF THE EMBODIMENTS

Figure 1:
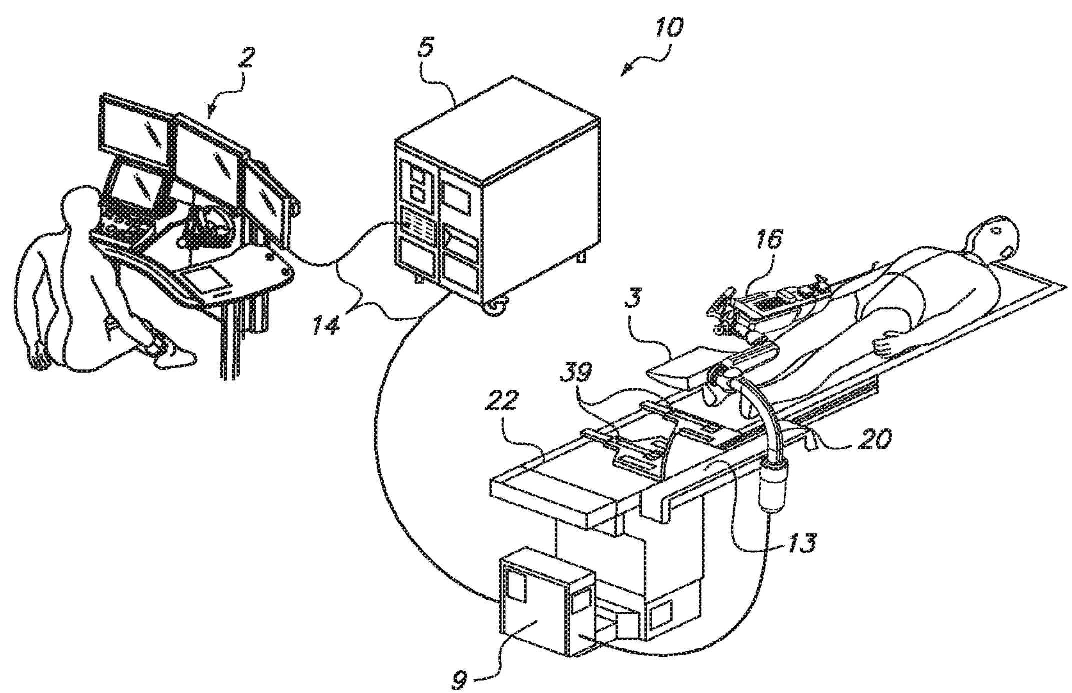
FIG. 1 illustrates a robotic surgical system in which apparatus, system and method embodiments may be implemented.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

I. Robotic System

Embodiments described herein generally relate to apparatus, systems and methods for robotic surgical systems. A robotic surgical system in which embodiments described herein may be implemented is described with reference to FIGS. 1-10C.

Referring to FIG. 1, a robotically controlled surgical system 10 in which embodiments of apparatus, system and method may be implemented includes an operator workstation 2, an electronics rack 6 and associated bedside electronics box 9, a setup joint or support assembly 20 (generally referred to as "support assembly"), and a robotic instrument driver 16 (generally referred to as "instrument driver"). A surgeon is seated at the operator workstation 2 and can monitor the surgical procedure, patient vitals, and control one or more robotic surgical devices.

Figure 2:
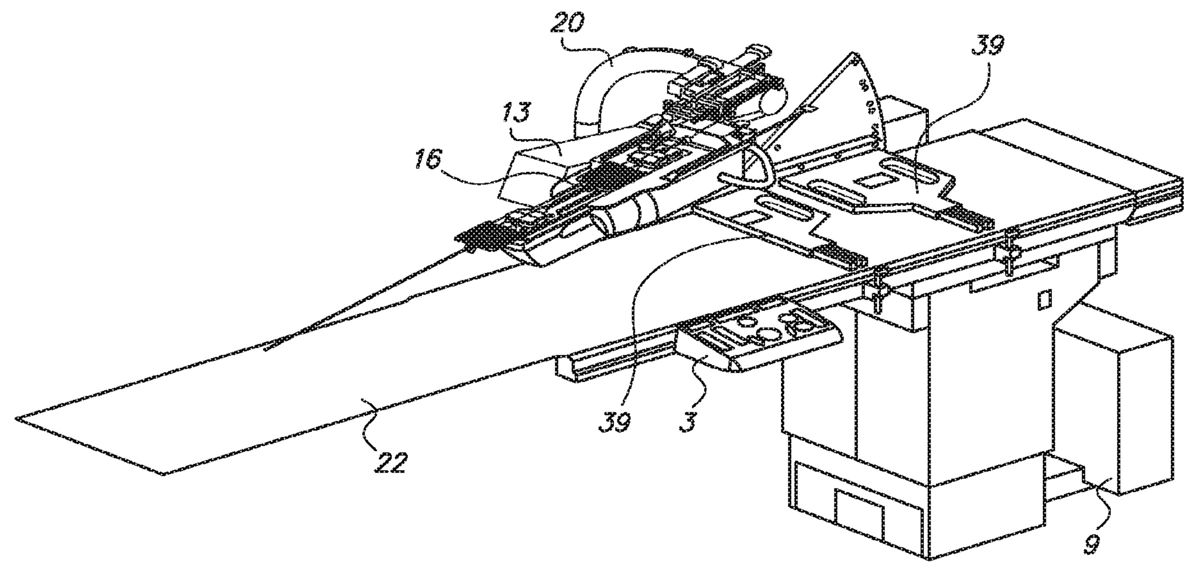
FIG. 2 illustrates how the adapter base plate assembly is utilized to attach a support assembly and instrument driver to an operating table or surgical bed.
Figure 3:
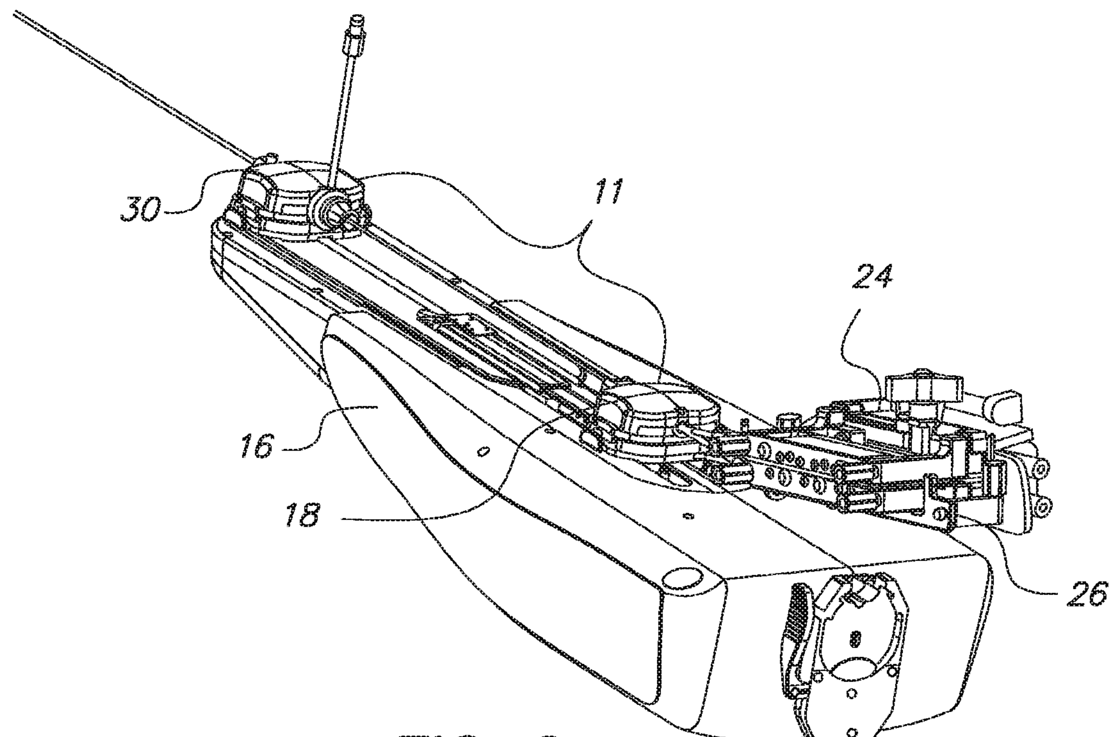
FIG. 3 a sheath and guide catheter assembly, and an elongate member manipulator mounted on an instrument driver

Referring to FIG. 2, the instrument driver 16, setup joint mounting brace 20, and bedside electronics box are shown in greater detail. Referring to FIG. 3, the instrument driver 16 is illustrated including an elongate member manipulator 24 and a robotic catheter assembly 11 installed. The robotic catheter assembly 11 includes a first or outer robotic steerable complement, otherwise referred to as a sheath instrument 30 (generally referred to as "sheath" or "sheath instrument") and/or a second or inner steerable component, otherwise referred to as a robotic catheter or guide or catheter instrument 18 (generally referred to as "catheter" or "catheter instrument"). The sheath instrument 30 and catheter instrument 18 are controllable using the instrument driver 16. During use, a patient is positioned on an operating table or surgical bed 22 (generally referred to as "operating table") to which the support assembly 20, instrument driver 16, and robotic catheter assembly 11 are coupled or mounted.

In the illustrated embodiments, the elongate member manipulator 24 (generally referred to as "manipulator") is configured for manipulating an elongate member 26. In some embodiments, the elongate member 26 may be a guidewire. In other embodiments, the elongate member 26 may be a treatment device (e.g., an ablation catheter) that is configured to deliver energy to treat tissue, such as tissue at a liver. In further embodiments, the elongate member 26 may be any of other instruments for medical use. During use, at least a part of the elongate member 26 is disposed within a lumen of the catheter instrument 18, and the proximal end of the elongate member 26 is removably coupled to the manipulator 24. In some embodiments, the manipulator 24 is configured to advance and retract the elongate member 26 relative to the catheter instrument 18. In other embodiments, the manipulator 24 may also be configured to roll the elongate member 26 so that it rotates about its longitudinal axis.

Various system components in which embodiments described herein may be implemented are illustrated in close proximity to each other in FIG. 1, but embodiments may also be implemented in systems 10 in which components are separated from each other, e.g., located in separate rooms. For example, the instrument driver 16, operating table 22, and bedside electronics box 9 may be located in the surgical area with the patient, and the operator workstation 2 and the electronics rack 6 may be located outside of the surgical area and behind a shielded partition. System 10 components may also communicate with other system 10 components via a network to allow for remote surgical procedures during which the surgeon may be located at a different location, e.g., in a different building or at a different hospital utilizing a communication link transfers signals between the operator control station 2 and the instrument driver 16. System 10 components may also be coupled together via a plurality of cables or other suitable connectors 14 to provide for data communication, or one or more components may be equipped with wireless communication components to reduce or eliminate cables 14. In this manner, a surgeon or other operator may control a surgical instrument while being located away from or remotely from radiation sources, thereby decreasing the operator's exposure to radiation.

Figure 4:
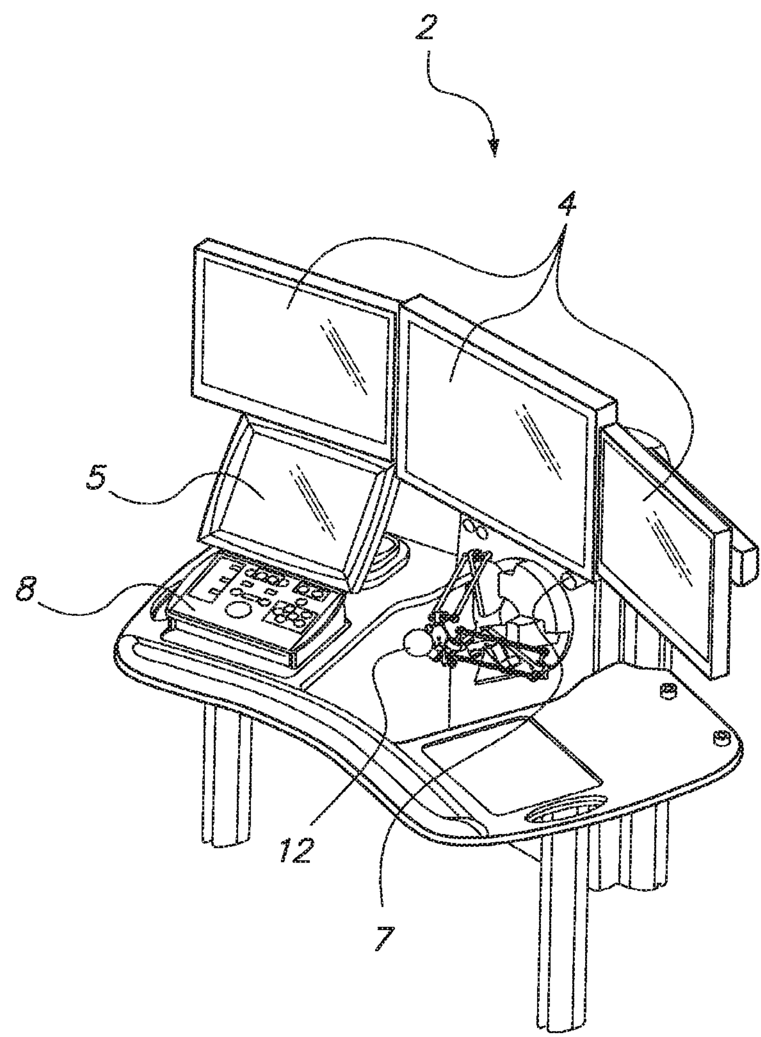
FIG. 4 illustrates an example of an operator workstation of the robotic surgical system shown in FIG. 1 with which a catheter instrument can be manipulated using different user interfaces and controls.

Referring to FIG. 4, one example of an operator workstation 2 that may be used with the system 10 shown in FIG. 1 includes three display screens 4, a touch screen user interface 5, a control button console or pendant 8, and a master input device (MID) 12. The MID 12 and pendant 8 serve as user interfaces through which the surgeon can control operation of the instrument driver 16 and attached instruments. By manipulating the pendant 8 and the MID 12, a surgeon or other operator can cause the instrument driver 16 to remotely control the catheter instrument 18 and/or the sheath instrument 30 mounted thereon. Also, in some embodiments, by manipulating one or more controls at the station 2, the surgeon or operator may cause the manipulator 24 to remotely move the elongate member 26. A switch 7 may be provided to disable activity of an instrument temporarily. The console 2 in the illustrated system 10 may also be configurable to meet individual user preferences. For example, in the illustrated example, the pendant 8 and the touch screen 5 are shown on the left side of the console 2, but they may also be relocated to the right side of the console 2. Various numbers of display screens may be provided. Additionally or alternatively, a bedside console 3 may be provided for bedside control of the of the instrument driver 16 if desired. Further, optional keyboard may be connected to the console 2 for inputting user data. The workstation 2 may also be mounted on a set of casters or wheels to allow easy movement of the workstation 2 from one location to another, e.g., within the operating room or catheter laboratory. Further aspects of examples of suitable MID 12, and workstation 2 arrangements are described in further detail in U.S. patent application Ser. No. 11/481,433, issued as U.S. Pat. No. 8,052,636 on Nov. 8, 2011, and U.S. Provisional Patent Application No. 60/840,331, the contents of which were previously incorporated herein by reference.

As shown in FIG. 1, the support assembly 20 is configured for supporting or carrying the instrument driver 16 over the operating table 22. One suitable support assembly 20 has an arcuate shape and is configured to position the instrument driver 16 above a patient lying on the table 22. The support assembly 20 may be configured to movably support the instrument driver 16 and to allow convenient access to a desired location relative to the patient. The support assembly 20 may also be configured to lock the instrument driver 16 into a certain position.

In the illustrated example, the support assembly 20 is mounted to an edge of the operating table 22 such that a catheter and sheath instruments 18, 30 mounted on the instrument driver 16 can be positioned for insertion into a patient. The instrument driver 16 is controllable to maneuver the catheter and/or sheath instruments 18, 30 within the patient during a surgical procedure. The distal portion of the setup joint 20 also includes a control lever 33 for maneuvering the setup joint 20. Although the figures illustrate a single guide catheter 18 and sheath assembly 30 mounted on a single instrument driver 16, embodiments may be implemented in systems 10 having other configurations. For example, embodiments may be implemented in systems 10 that include a plurality of instrument drivers 16 on which a plurality of catheter/sheath instruments 18, 30 can be controlled. Further aspects of a suitable support assembly 20 are described in U.S. patent application Ser. No. 11/481,433, issued as U.S. Pat. No. 8,052,636 on Nov. 8, 2011, and U.S. Provisional Patent Application No. 60/879,911, the contents of which are expressly incorporated herein by reference. Referring to FIG. 2, the support assembly 20 may be mounted to an operating table 22 using a universal adapter base plate assembly 39, similar to those described in detail in U.S. Provisional Patent Application No. 60/899,048, incorporated by reference herein in its entirety. The adapter plate assembly 39 mounts directly to the operating table 22 using clamp assemblies, and the support assembly 20 may be mounted to the adapter plate assembly 39. One suitable adapter plate assembly 39 includes two large, flat main plates which are positioned on top of the operating table 22. The assembly 39 provides for various adjustments to allow it to be mounted to different types of operating tables 22. An edge of the adapter plate assembly 39 may include a rail that mimics the construction of a traditional surgical bedrail. By placing this rail on the adapter plate itself, a user may be assured that the component dimensions provide for proper mounting of the support assembly 20. Furthermore, the large, flat surface of the main plate provides stability by distributing the weight of the support assembly 20 and instrument driver 16 over an area of the table 22, whereas a support assembly 20 mounted directly to the operating table 22 rail may cause its entire load to be placed on a limited and less supportive section of the table 22. Additionally or alternatively, a bedside rail 13 may be provided which may couple the support assembly 20 to the operating table 22. The bedside rail may include a leadscrew mechanism which will enable the support assembly to translate linearly along the edge of the bed, resulting in a translation of the instrument driver 16 and ultimately a translation in the insert direction of the catheter and sheath instruments 18/30.

Figure 5A:
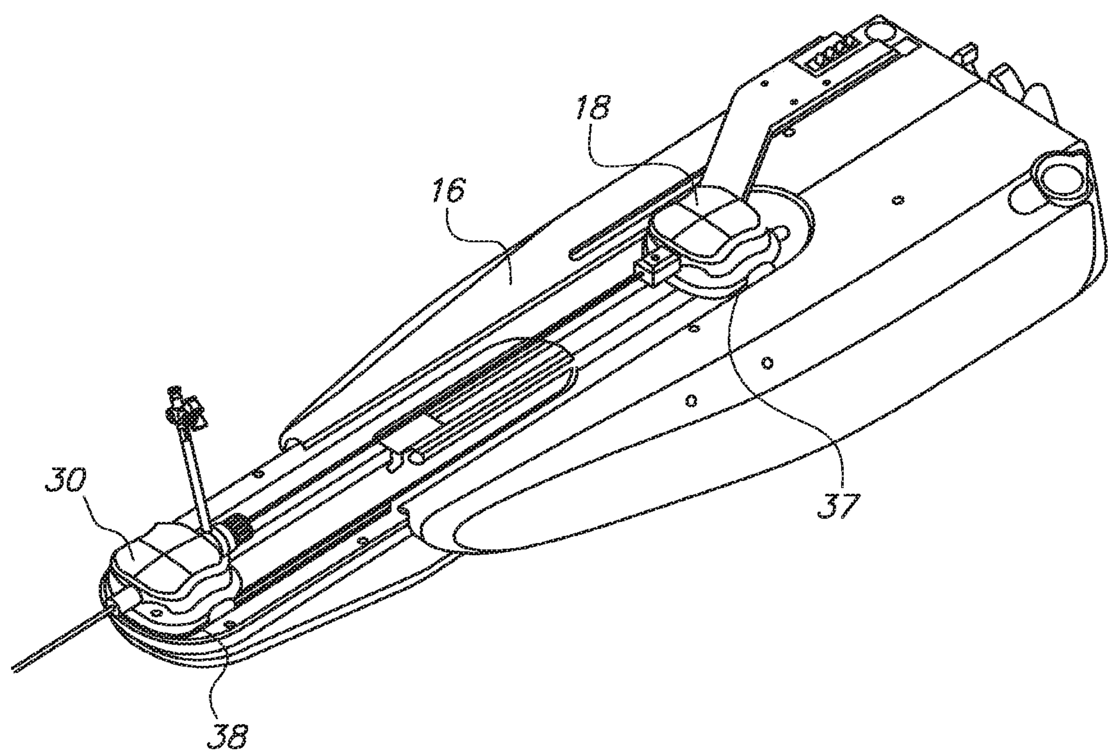
FIG. 5A further illustrates the instrument driver shown in FIG. 3 without the elongate member manipulator mounted on an instrument driver.
Figure 5B:
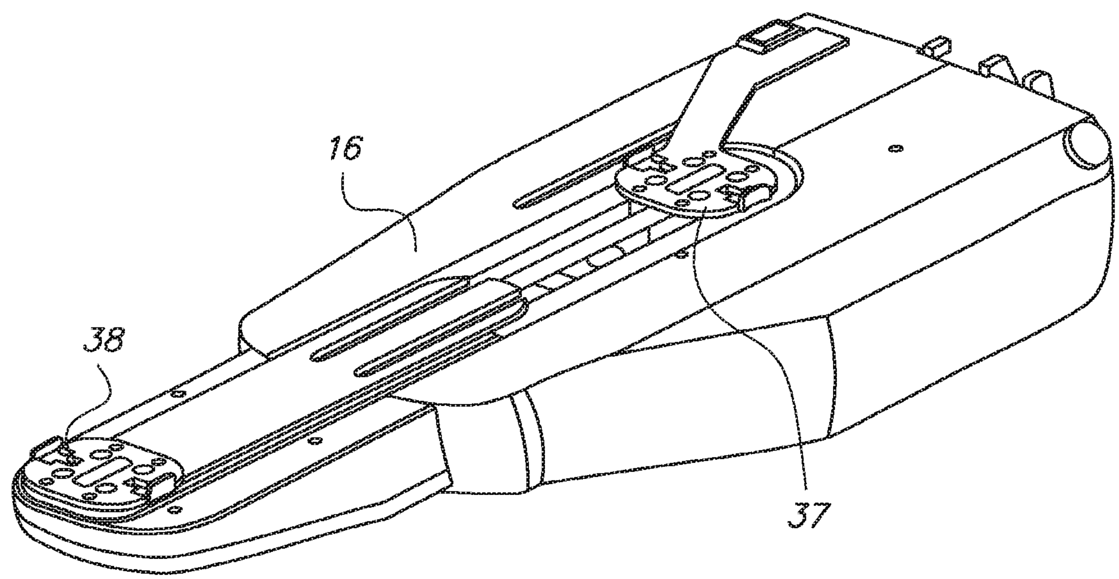
FIG. 5B further illustrates the instrument driver shown in FIG. 5A without the sheath and guide catheter assembly.
Figure 5C:
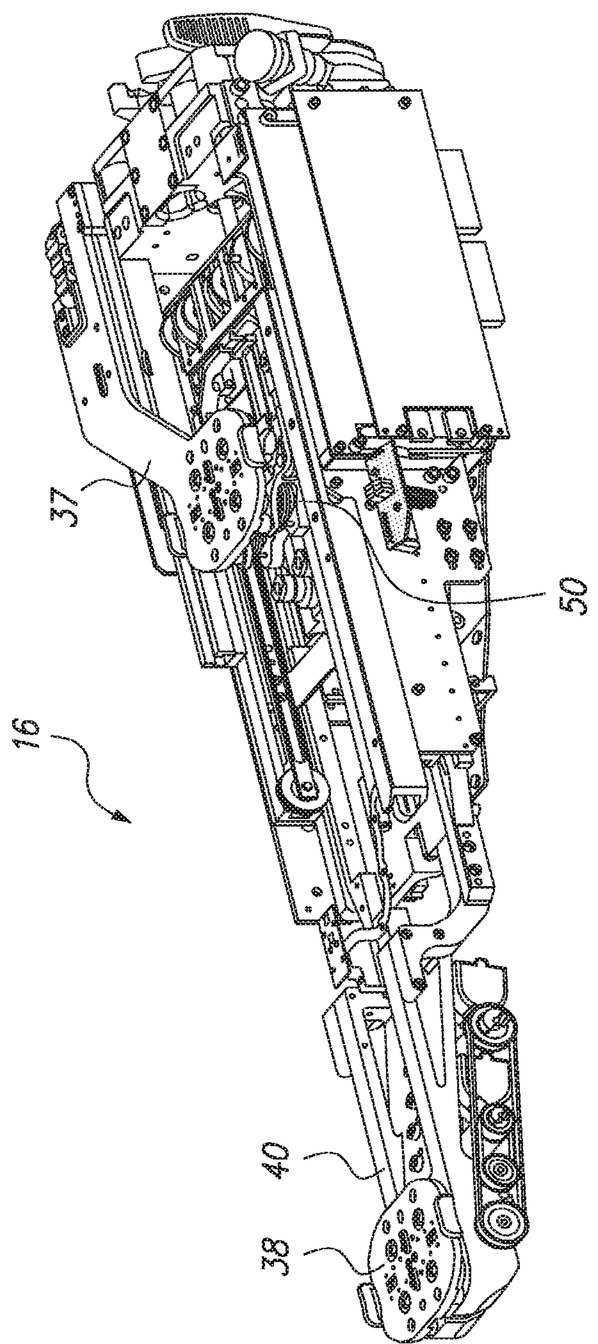
FIG. 5C further illustrates the instrument driver shown in FIG. 5B with skins removed.

FIGS. 5A-C illustrate the instrument drive 16 with various components installed. FIG. 5A illustrates the instrument driver 16 with the instrument assembly 11 installed including the sheath instrument 30 and the associated guide or catheter instrument 18 while FIG. 5B illustrates the instrument driver 16 without an attached instrument assembly 11. The sheath instrument 30 and the associated guide instrument 18 are mounted to associated mounting plates 37, 38 on a top portion of the instrument driver 16. FIG. 5C illustrates the instrument driver 16 with skins removed to illustrate internal components. Embodiments described are similar to those described in detail in U.S. patent application Ser. Nos. 11/678,001, issued as U.S. Pat. No. 8,092,397 on Jan. 10, 2012, 11/678,016, issued as U.S. Pat. No. 8,052,621 on Nov. 8, 2011, and 11/804,585, now abandoned, each incorporated by reference herein in its entirety.

Figure 6A:
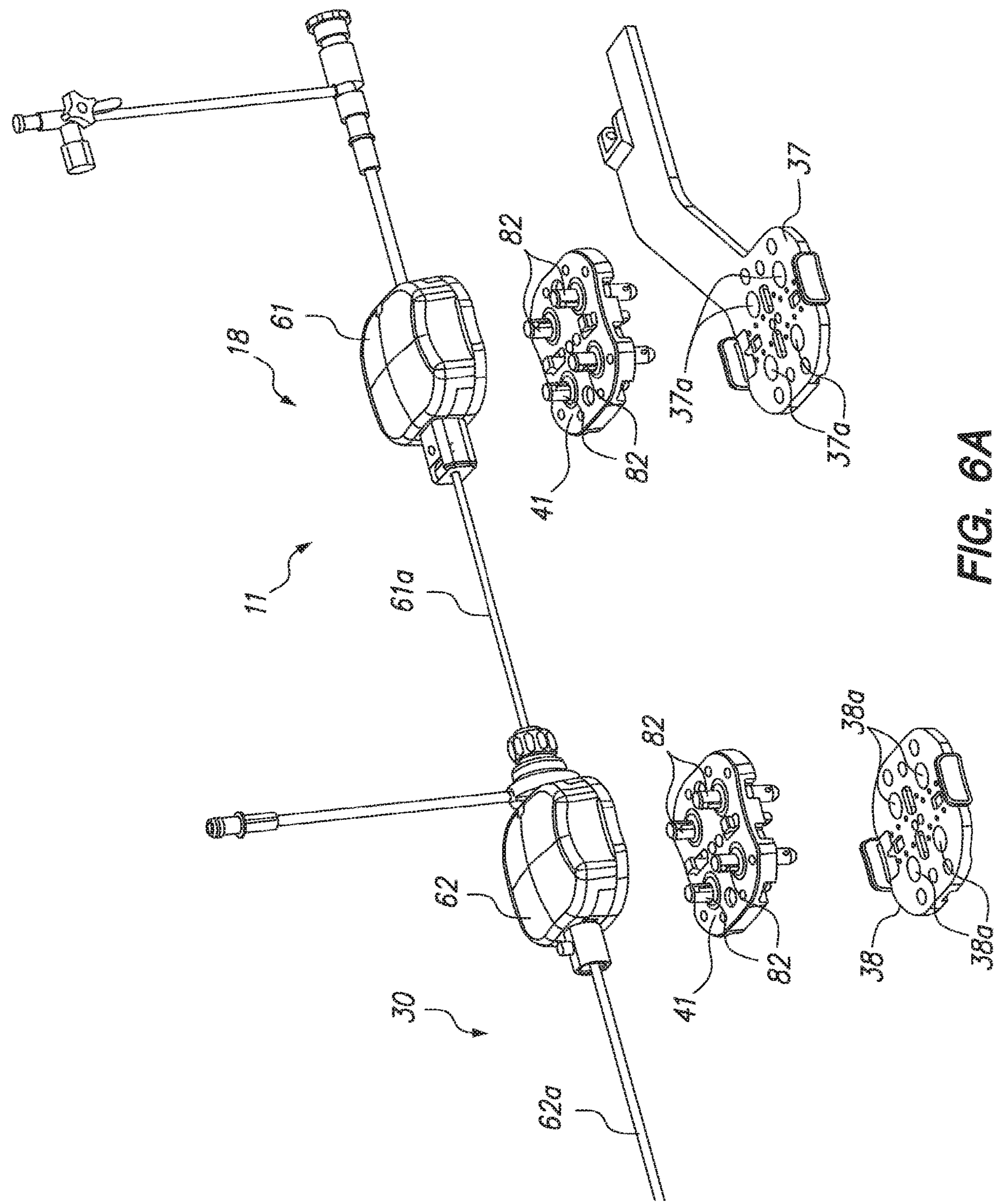
FIGS. 6A and 6B illustrate a sheath and guide catheter assembly positioned over respective sterile adaptors and mounting plates from top and bottom perspectives respectively
Figure 6B:
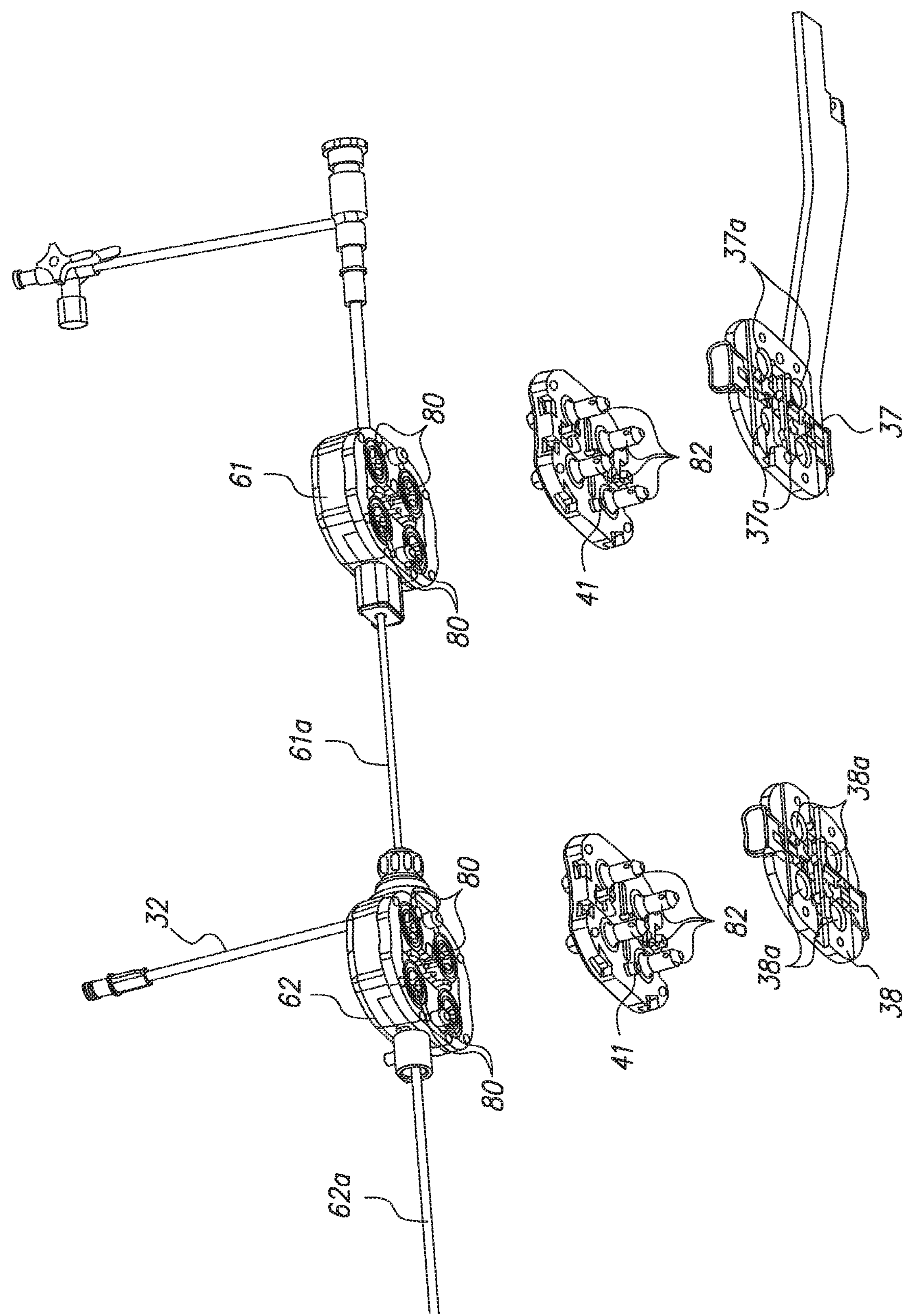

Referring to FIGS. 6A-B, the assembly 11 that includes the sheath instrument 30 and the guide or catheter instrument 18 positioned over their respective mounting plates 38, 37 is illustrated removed from the instrument driver 16. Additionally a sterile adaptor 41 can be used to couple each of the sheath and guide instruments to their respective mounting plates. The catheter instrument 18 includes a guide catheter instrument member 61*a*, and the sheath instrument 30 includes a sheath instrument member 62*a*. The guide catheter instrument member 61*a* is coaxially interfaced with the sheath instrument member 62*a* by inserting the guide catheter instrument member 61*a* into a working lumen of the sheath catheter member 62*a*. As shown in FIG. 6A, the sheath instrument 30 and the guide or catheter instrument 18 are coaxially disposed for mounting onto the instrument driver 16. However, it should be understood that the sheath instrument 16 may be used without a guide or catheter instrument 18, or the guide or catheter instrument 18 may be used without a sheath instrument 30. In such cases, the sheath instrument 16 or the catheter instrument 18 may be mounted onto the instrument driver 16 individually. With the coaxial arrangement as shown in FIG. 6A, a guide catheter splayer 61 is located proximally relative to, or behind, a sheath splayer 62 such that the guide catheter member 61*a* can be inserted into and removed from the sheath catheter member 61*b*.

The splayers 61, 62 are configured to steer the members 61*a*, 61*b*, respectively. In the illustrated embodiments, each of the splayers 61, 62 includes drivable elements therein configured to apply tension to different respective wires inside the member 61*a*/61*b* to thereby steer the distal end of the member 61*a*/61*b*. In some embodiments, the drivable elements may be actuated in response to a control signal from a controller, which receives an input signal from the work station 2, and generates the control signal in response to the input signal. Also, in the illustrated embodiments, the splayers 61, 62 may be translated relative to the instrument driver 16. In some embodiments, the instrument driver 16 may be configured to advance and retract each of the splayers 61, 62, so that the catheter instrument 18 and the sheath instrument 30 may be advanced distally and retracted proximally.

Figure 7A:
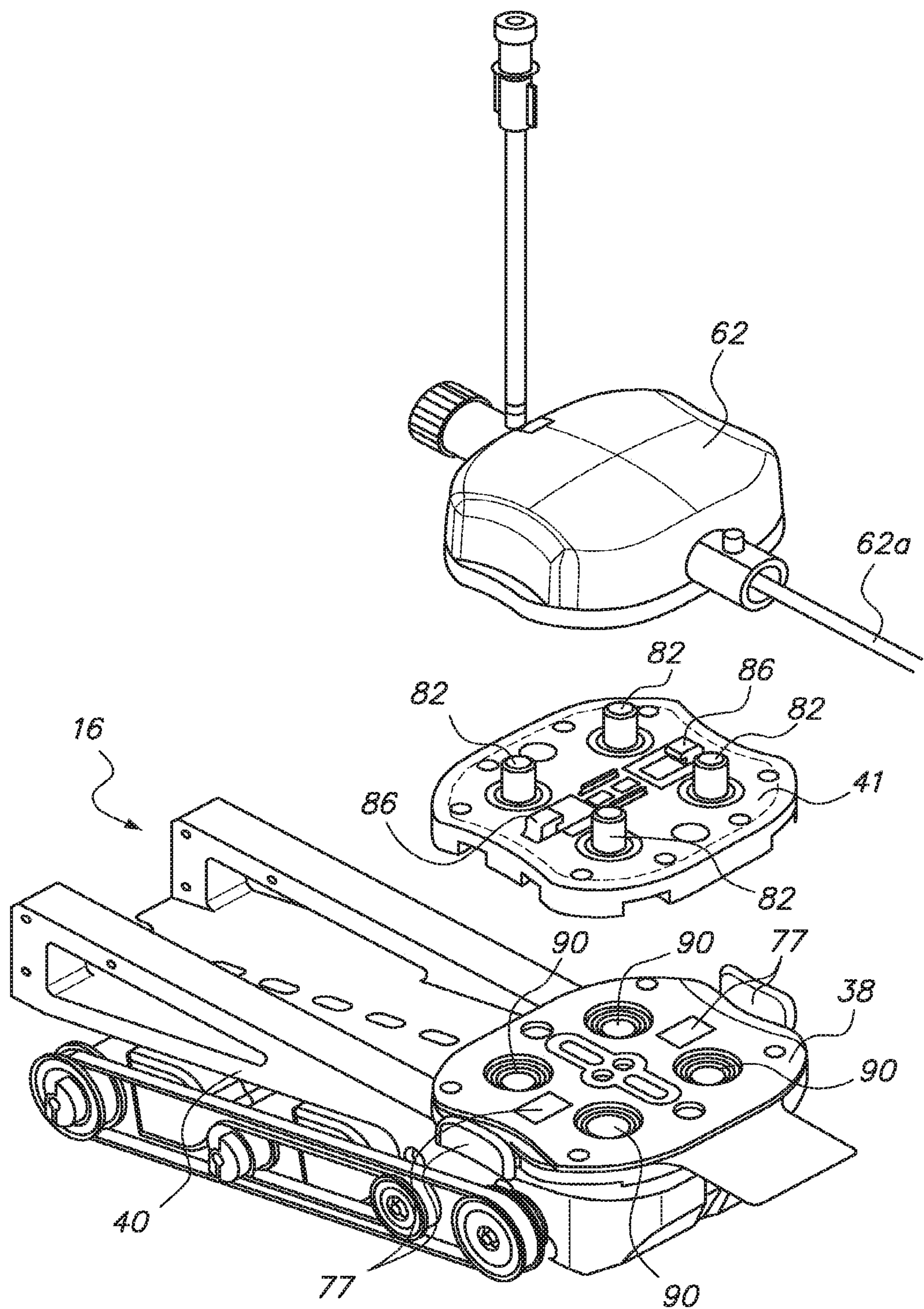
FIGS. 7A and 7B illustrate top and bottom perspectives respectively of a portion of an instrument driver with a sheath splayer positioned over a sterile adaptor.
Figure 7B:
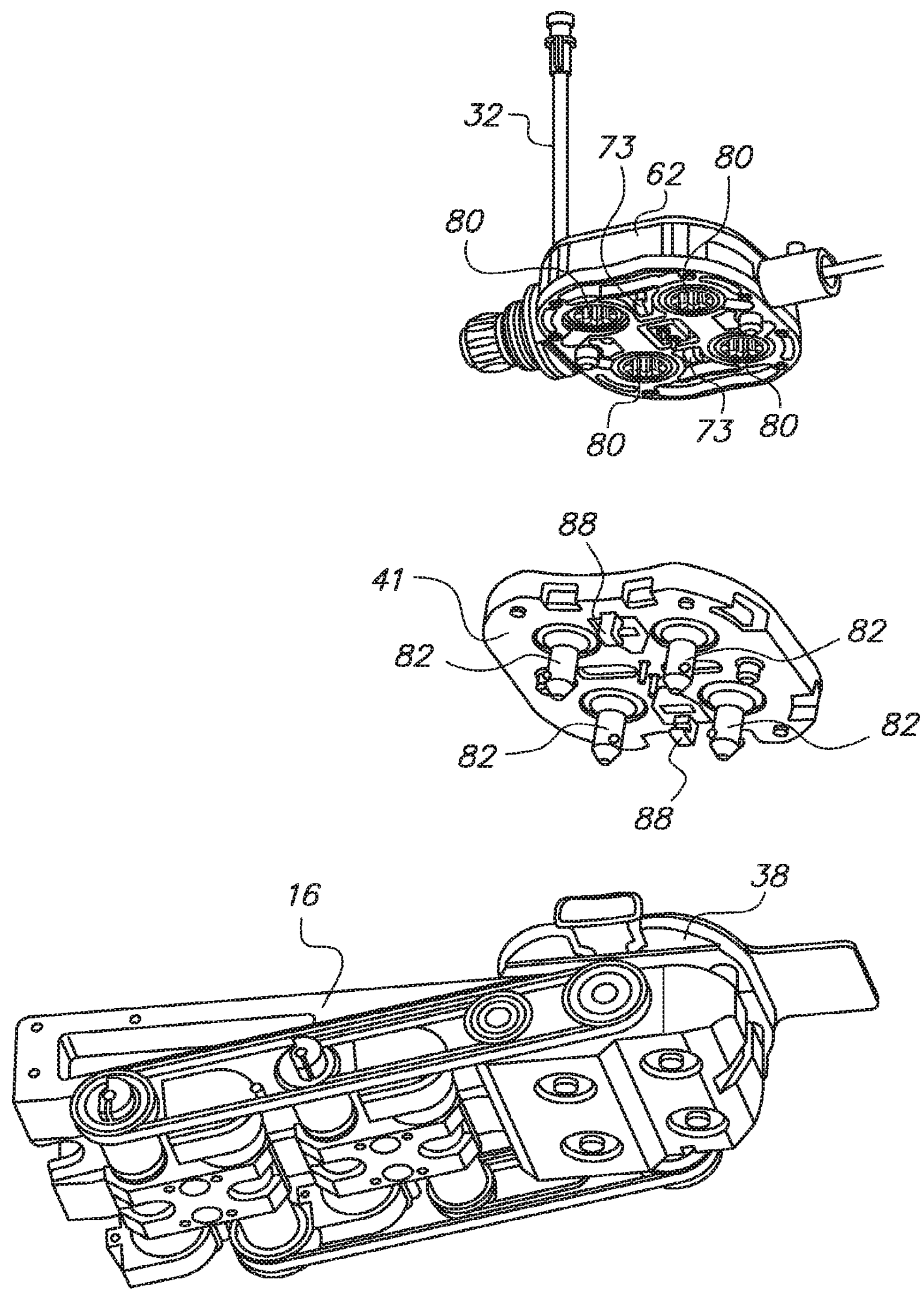

FIGS. 7A and 7B illustrate the sheath splayer 62 of one embodiment illustrated with the sterile adaptor 41 and mounting plate 38 coupled to a portion of the instrument driver shown with only a set of actuation mechanisms that will be described later in detail. As shown in FIG. 6A, the sheath and guide splayers 62, 61, appear similar physically in construction with the exception of differences in a valve purge tube 32. It should be noted that the purge tube 32 may or may not be included for either the guide or sheath splayer. The sheath splayer 62 will be described herein. However it should be understood that the guide splayer 61 is of similar construction, and components of the sheath splayer 62 can be repeated for the guide splayer 61.

Figure 7C:
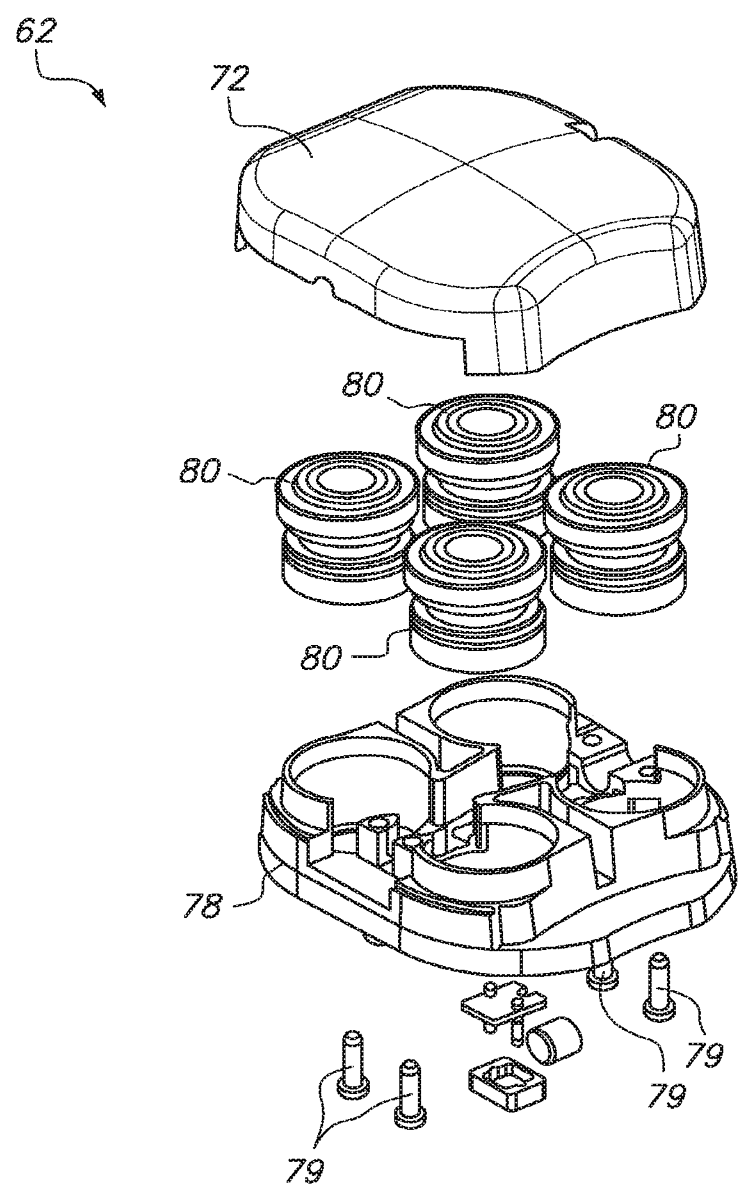
FIG. 7C illustrates an exploded view of the sheath splayer shown in FIG. 7A without a purge tube.

As illustrated in FIG. 7C, the splayer 62 includes a splayer cover 72 fixably coupled to a splayer base assembly 78 using four screws 79. The splayer base 78 having four cavities to receive and house pulley assemblies 80 is used for both the guide splayer 61 and sheath splayer 62. For this embodiment of a sheath splayer 62, four cavities of the splayer base 78 are populated with pulley assemblies 80 but it should be understood that varying numbers of cavities may be populated leaving remaining cavities open. The guide splayer 61 may have all its cavities populated with four pulley assemblies 80 for pulling four respective wires, as can be seen in FIG. 6B. The splayer base 78 of this implementation can be constructed from injection molded polycarbonate.

During splayer 62 assembly, the pulley assembly 80 is put together and mated with a catheter pull wire or control element (not shown). The pull wire (not shown) runs down the length of a catheter from distal to proximal end then is wound about the pulley. By rotating the pulley, the pull wire bends the distal tip of the catheter controlling its bend.

Referring back to FIGS. 6A-6B, when a catheter is prepared for use with an instrument, its splayer is mounted onto its appropriate mounting plate via a sterile adaptor. In this case, the sheath splayer 62 is placed onto the sheath mounting plate 38 and the guide splayer 61 is place onto the guide mounting plate 37 via sterile adaptors 41. Referring to FIG. 7A-B, the pulley assemblies 80 are configured to couple to floating shafts 82 on the splayer adaptor 41 which in turn are configured to couple to sleeve receptacles 90. In the illustrated example, each mounting plates 37, 38 has four openings 37*a*, 38*a* that are designed to receive the corresponding floating shafts 84 attached to and extending from the sterile adaptors 41 coupled to the splayers 61, 62. In the example illustrated in FIG. 6B, four floating shafts 82 of the sterile adaptor 41 are insertable within the openings 38*a* of the sheath mounting plate 38 as the splayer 62 is mounted onto the RCM. Similarly, four floating shafts 82 of the sterile adaptor 41 are insertable within the four apertures or openings 37*a* of the guide interface plate 37. Referring to FIGS.

Figure 7D:
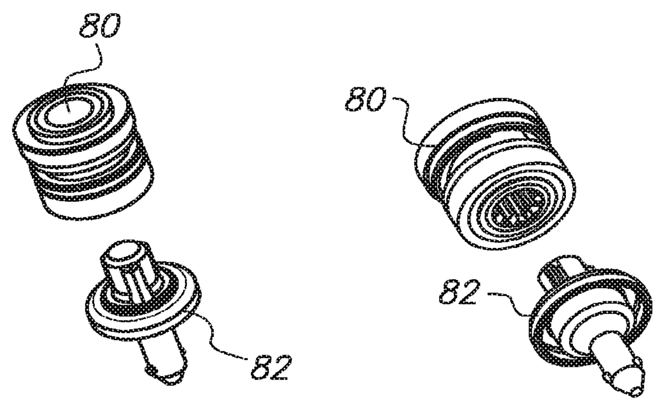
FIG. 7D illustrates top and bottom views of a pulley assembly positioned over a floating shaft.
Figure 7E:
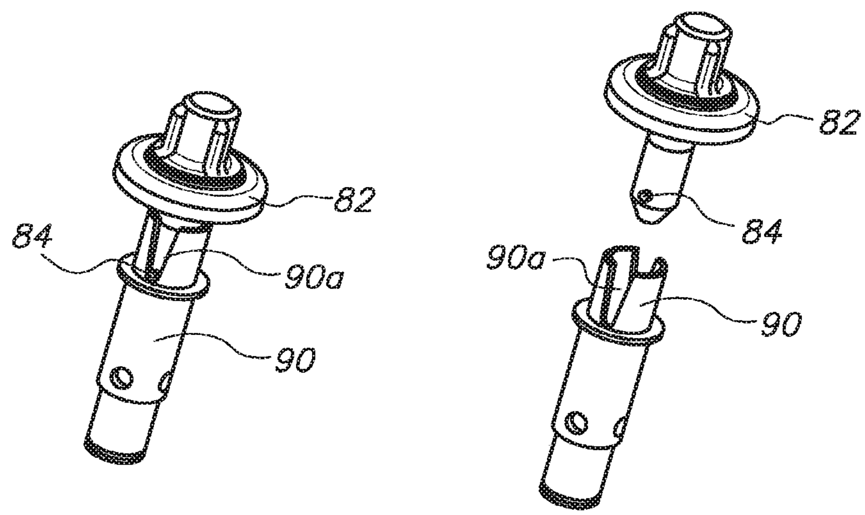
FIG. 7E illustrates the floating shaft of FIG. 7D installed and un-installed onto a sleeve receptacle.

7D-E, the coupling of the pulley assemblies 80 to floating shafts 82 and floating shafts 82 to sleeve receptacles 90 is illustrated. FIG. 7D illustrates top and bottom perspective views of the pulley assembly 80 positioned above the floating shaft 82 where the bottom of the pulley assembly 80 is configured to mate with splines on the top of the floating shaft 82. FIG. 7E illustrates the floating shaft 82 installed and un-installed onto the sleeve receptacle 90. The sleeve receptacles can include a notch 90*a* shaped to accept a pin 84 on the floating shaft 82.

Referring back to FIGS. 7A-B, the sheath splayer 62 is shown having latches 73 which may couple to hooks 86. By depressing the latches 73, the splayer 62 may be locked and unlocked to the sterile adaptor 41. The sterile adaptor in turn is configured having mounting hooks 88 which couple to sliding latches 77 on the mounting plate 83. The sliding latches 77 can be spring loaded to allow the adaptor plate 41 to be locked to the mounting plate 38 by applying downward force on the adaptor plate 41. The sliding latches can be depressed to release the adaptor plate 41 when desired.

The sheath interface mounting plate 38 as illustrated in FIGS. 6A and 6B is similar to the guide interface mounting plate 37, and thus, similar details are not repeated. One difference between the plates 37, 38 may be the shape of the plates. For example, the guide interface plate 37 includes a narrow, elongated segment, which may be used with, for example, a dither mechanism or the elongate member manipulator 24. Both plates 37, 38 include a plurality of openings 37*a*, 38*a* to receive floating shafts 82 and latches 73 from sterile adaptors 41. The splayers 61/62, sterile adaptors 41, and mounting plates 37/38 are all described in greater detail in U.S. patent application Ser. No. 13/173,994, filed on Jun. 30, 2011, issued as U.S. Pat. No. 8,827,948 on Sep. 9, 2014, the entire disclosure of which is expressly incorporated by reference herein.

Figure 8:
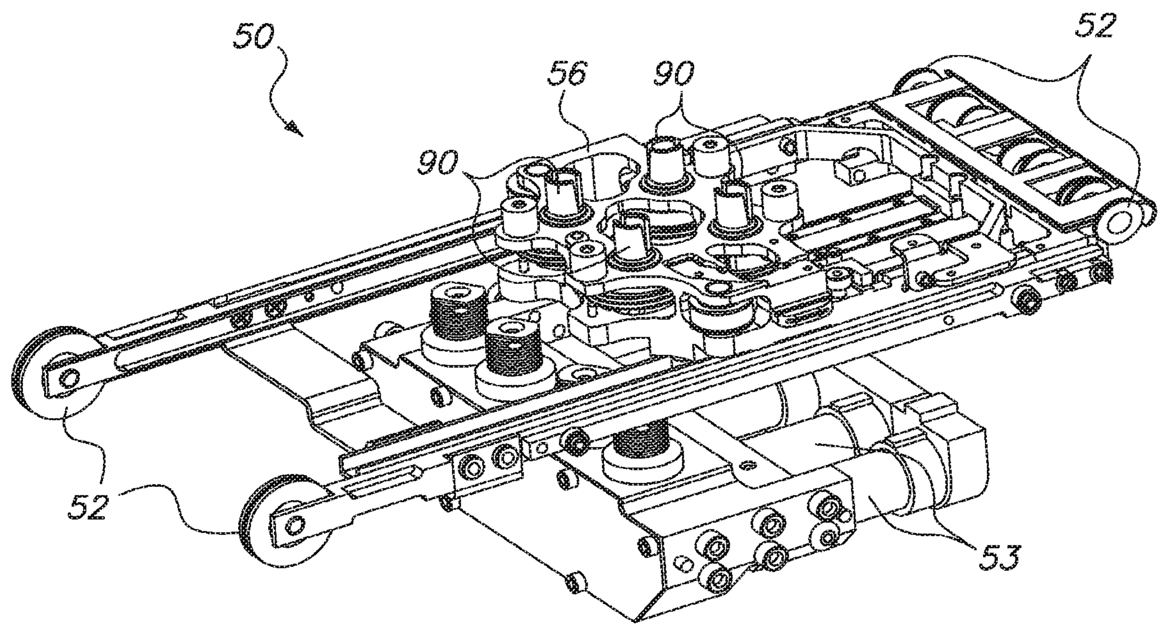
FIG. 8 illustrates a guide carriage of the instrument driver shown in FIG. 5C with pulleys and guide articulation motors.
Figure 9:
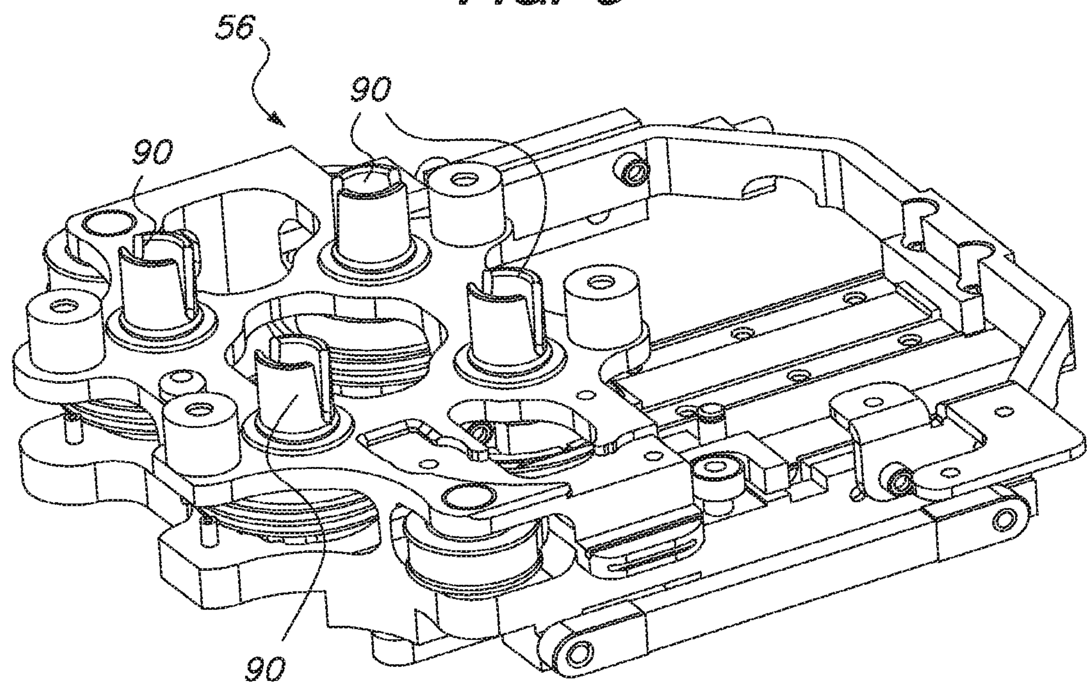
FIG. 9 is a perspective view of a slidable carriage or funicular assembly of an instrument driver and sleeve receptacles configured to receive and engage with floating shafts.

Referring back to FIG. 5C the instrument driver 16 is illustrated with mounting plates 37,38 fixably coupled to a guide carriage 50, and a sheath drive block 40, respectively. FIG. 8 illustrates the guide carriage 50 removed from the instrument driver 16 coupled to cabling (not shown) and associated guide motors 53. The guide carriage 50 includes a funicular assembly 56 which is illustrated in FIG. 9. The funicular assembly 56 includes the four sleeve receptacles 90. As previously described, the floating shafts 82 of the sterile adaptor 41 first insert through the openings 37*a* in the mounting plate 37. They then engage with the sleeve receptacles 90

Referring back to FIG. 8, a set of cables (not shown) wound around a set of pulleys 52, are coupled on one end to a set of guide motors 53 and the other end to the sleeve receptacles 90. Note that only two of four motors can be seen in FIG. 8. The drive motors 53 are actuated to rotationally drive the sleeves 90. The catheter assembly 18 with its splayer 61 mounted onto the instrument drive 16 would have its pulley assemblies 80 coupled to corresponding sleeves 90 via floating shafts 82. As the sleeves 90 are rotated, the pins 84 of the floating shafts 82 are seated in the V-shaped notches and are engaged by the rotating sleeves 90, thus causing the floating shafts 82 and associated pulley assemblies 80 to also rotate. The pulley assemblies 80 in turn cause the control elements (e.g., wires) coupled thereto to manipulate the distal tip of the catheter instrument 30 member in response thereto. FIGS. 10A and 10B illustrate top and bottom perspective views of the sheath output plate 38 exploded from the sheath block 40 and motor driven interfaces 42 which are coupled to sheath articulation motors 43. FIG. 10C illustrates sheath articulation motors 43 coupled to the motor driven interfaces 42 which includes a set of belts, shafts, and gears which drive receptacle sleeves 90 (which are similar in construction and functionality to the receptacle sleeves previously described for the guide funicular assembly). When the sheath splayer pulley assemblies 80 and sterile adaptor floating shafts 82 are coupled to the receptacle sleeves 90, the sheath articulation motors 43 drive the receptacle sleeves 90 causing the sheath instrument 30 to bend in the same manner described for the guide instrument.

Figure 10:
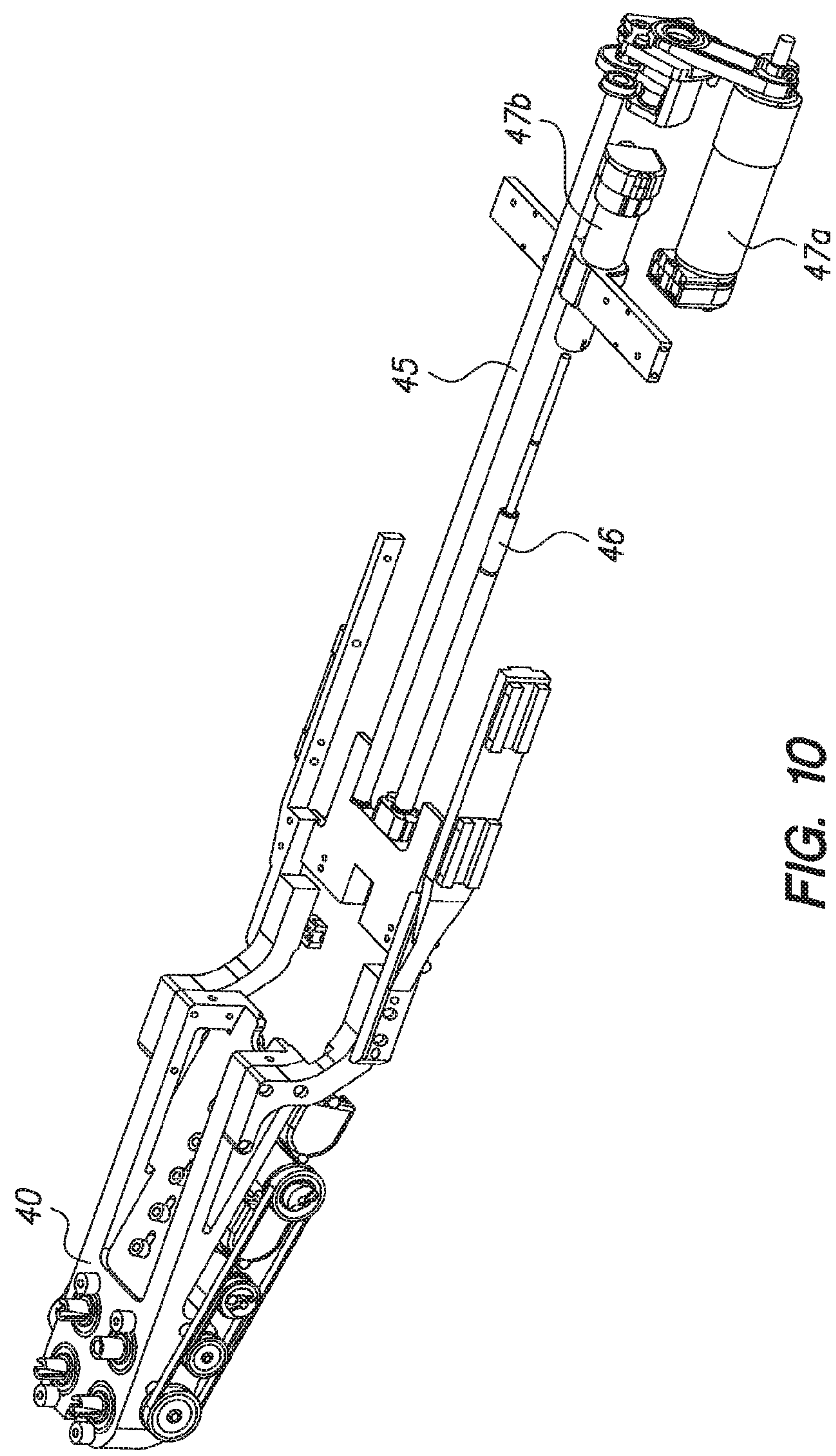
FIG. 10 illustrates a sheath block, sheath insert motor, guide insert motor and leadscrews removed from the instrument driver shown in FIG. 5C.

During use, the catheter instrument 18 is inserted within a central lumen of the sheath instrument 30 such that the instruments 18, 30 are arranged in a coaxial manner as previously described. Although the instruments 18, 30 are arranged coaxially, movement of each instrument 18, 30 can be controlled and manipulated independently. For this purpose, motors within the instrument driver 16 are controlled such that the drive and sheath carriages coupled to the mounting plates 37, 38 are driven forwards and backwards independently on linear bearings each with leadscrew actuation. FIG. 10 illustrates the sheath drive block 40 removed from the instrument driver coupled to two independently-actuated lead screw 45, 46 mechanisms driven by guide and sheath insert motors 47*a*,47*b*. Note the guide carriage is not shown. In the illustrated embodiment, the sheath insertion motor 47*b* is coupled to a sheath insert leadscrew 46 that is designed to move the sheath articulation assembly forwards and backwards, thus sliding a mounted sheath catheter instrument (not shown) forwards and backwards. The insert motion of the guide carriage can be actuated with a similar motorized leadscrew actuation where a guide insert motor 47*a* is coupled to the guide insert leadscrew 45 via a belt.

Referring back to FIGS. 1, 4 and 6A, in order to accurately steer the robotic sheath 62*a* or guide catheter 61*a* from an operator work station 2, a control structure may be implemented which allows a user to send commands through input devices such as the pendant 8 or MID 12 that will result in desired motion of the sheath 62*a* and guide 61*a*. In some embodiments, the sheath 62*a* and/or the guide 61*a* may each have four control wires for bending the instrument in different directions. Referring to FIGS. 11A-H, the basic kinematics of a catheter 120 with four control elements 122*a*, 122*b*, 122*c*, 122*d* is shown. The catheter 120 may be component 61*a* or component 62*a* in some embodiments. Referring to FIGS. 11A-B, as tension is placed only upon the bottom control element 122*c*, the catheter bends downward, as shown in FIG. 11A. Similarly, pulling the left control element 122*d* in FIGS. 11C-D bends the catheter left, pulling the right control element 122*b* in FIGS. 11E-F bends the catheter right, and pulling the top control element 122*a* in FIGS. 11G-H bends the catheter up. As will be apparent to those skilled in the art, well-known combinations of applied tension about the various control elements results in a variety of bending configurations at the tip of the catheter member 120.

The kinematic relationships for many catheter instrument embodiments may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and − directions. Other motorized tension relationships may drive other instruments, active tensioning, or insertion or roll of the catheter instrument. The relationship between actuated inputs and the catheter's end point position as a function of the actuated inputs is referred to as the "kinematics" of the catheter.

To accurately coordinate and control actuations of various motors within an instrument driver from a remote operator control station such as that depicted in FIG. 1, a computerized control and visualization system may be employed. The control system embodiments that follow are described in reference to a particular control systems interface, namely the SimuLink™ and XPC™ control interfaces available from The Mathworks Inc., and PC-based computerized hardware configurations. However, one of ordinary skilled in the art having the benefit of this disclosure would appreciate that many other control system configurations may be utilized, which may include various pieces of specialized hardware, in place of more flexible software controls running on one or more computer systems.

Figure 12:
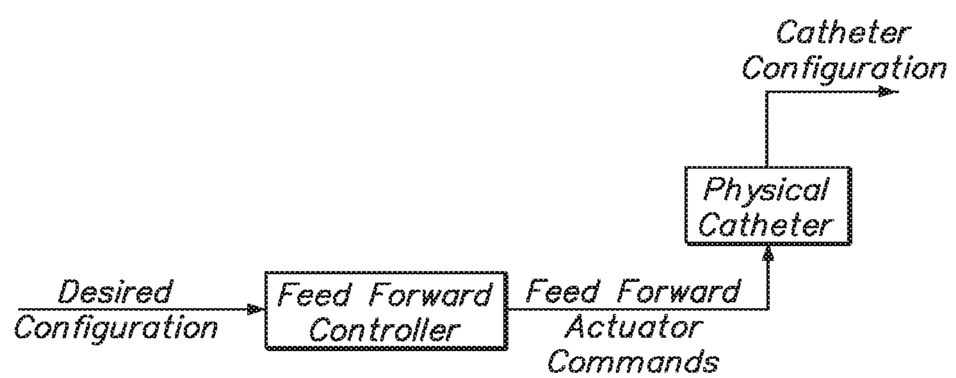
FIG. 12 illustrates an open loop control model.
Figure 13:
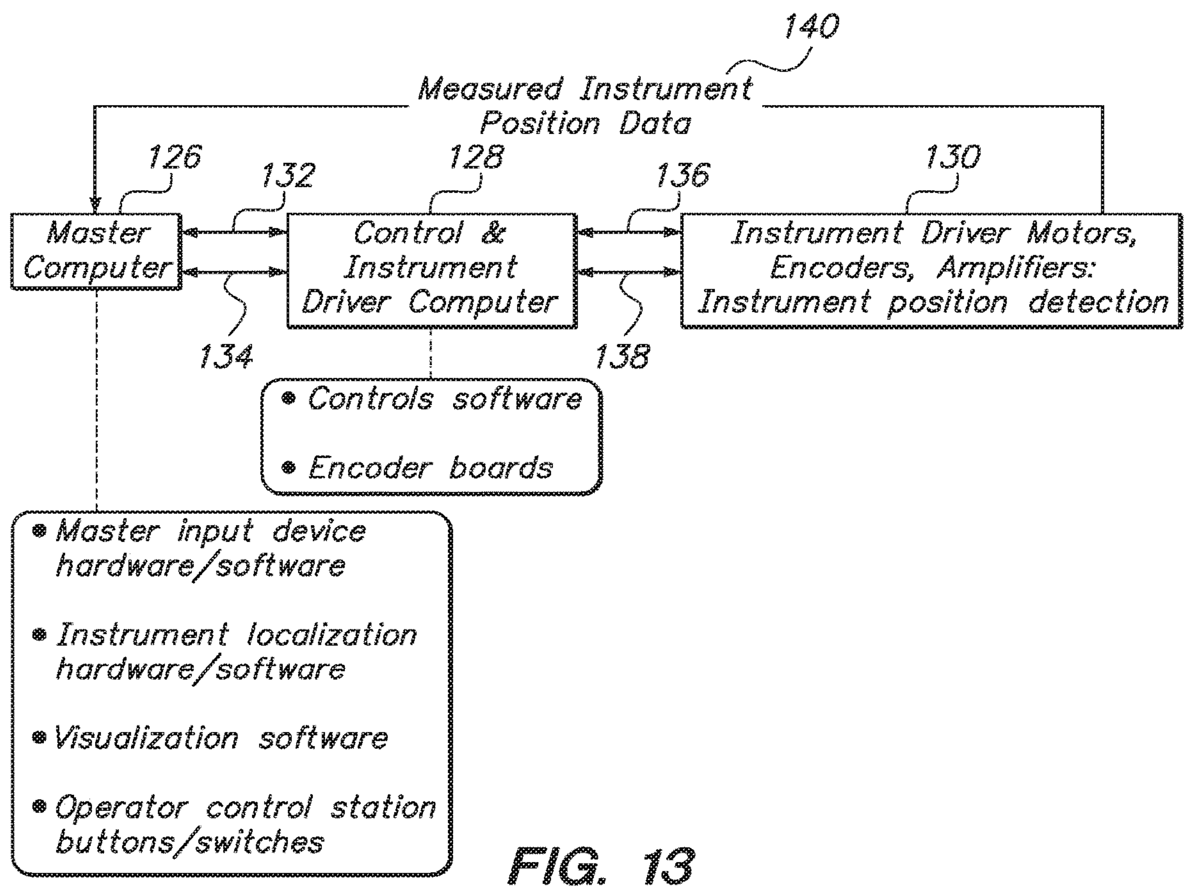
FIG. 13 illustrates a control system in accordance with some embodiments.

FIGS. 12-13 illustrate examples of a control structure for moving the catheter 61*a* and/or the sheath 62*a* in accordance with some embodiments. In one embodiment, the catheter (or other shapeable instrument) is controlled in an open-loop manner as shown in FIG. 12. In this type of open loop control model, the shape configuration command comes in to the beam mechanics, is translated to beam moments and forces, then is translated to tendon tensions given the actuator geometry, and finally into tendon displacement given the entire deformed geometry.

Referring to FIG. 13, an overview of other embodiment of a control system flow is depicted. A master computer 400 running master input device software, visualization software, instrument localization software, and software to interface with operator control station buttons and/or switches is depicted. In one embodiment, the master input device software is a proprietary module packaged with an off-the-shelf master input device system, such as the Phantom™ from Sensible Devices Corporation, which is configured to communicate with the Phantom™ hardware at a relatively high frequency as prescribed by the manufacturer. Other suitable master input devices, such as the master input device 12 depicted in FIG. 2 are available from suppliers such as Force Dimension of Lausanne, Switzerland. The master input device 12 may also have haptics capability to facilitate feedback to the operator, and the software modules pertinent to such functionality may also be operated on the master computer 126.

Figure 14:
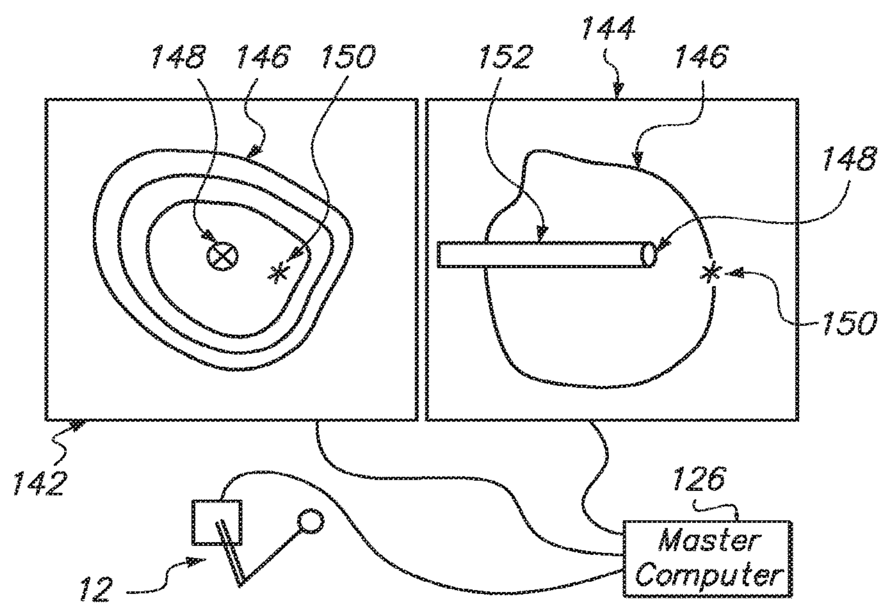
FIG. 14 illustrates a user interface for a master input device.

Referring to FIG. 13, in one embodiment, visualization software runs on the master computer 126 to facilitate real-time driving and navigation of one or more steerable instruments. In one embodiment, visualization software provides an operator at an operator control station, such as that depicted in FIG. 2, with a digitized "dashboard" or "windshield" display to enhance instinctive drivability of the pertinent instrumentation within the pertinent tissue structures. Referring to FIG. 14, a simple illustration is useful to explain one embodiment of a preferred relationship between visualization and navigation with a master input device 12. In the depicted embodiment, two display views 142, 144 are shown. One preferably represents a primary 142 navigation view, and one may represent a secondary 144 navigation view. To facilitate instinctive operation of the system, it is preferable to have the master input device coordinate system at least approximately synchronized with the coordinate system of at least one of the two views. Further, it is preferable to provide the operator with one or more secondary views which may be helpful in navigating through challenging tissue structure pathways and geometries.

Referring still to FIG. 14, if an operator is attempting to navigate a steerable catheter in order to, for example, contact a particular tissue location with the catheter's distal tip, a useful primary navigation view 142 may comprise a three dimensional digital model of the pertinent tissue structures 146 through which the operator is navigating the catheter with the master input device 12, along with a representation of the catheter distal tip location 148 as viewed along the longitudinal axis of the catheter near the distal tip. This embodiment illustrates a representation of a targeted tissue structure location 150, which may be desired in addition to the tissue digital model 146 information. A useful secondary view 144, displayed upon a different monitor, in a different window upon the same monitor, or within the same user interface window, for example, comprises an orthogonal view depicting the catheter tip representation 148, and also perhaps a catheter body representation 152, to facilitate the operator's driving of the catheter tip toward the desired targeted tissue location 150.

In one embodiment, subsequent to development and display of a digital model of pertinent tissue structures, an operator may select one primary and at least one secondary view to facilitate navigation of the instrumentation. By selecting which view is a primary view, the user can automatically toggle a master input device 12 coordinate system to synchronize with the selected primary view. In an embodiment with the leftmost depicted view 142 selected as the primary view, to navigate toward the targeted tissue site 150, the operator should manipulate the master input device 12 forward, to the right, and down. The right view will provide valued navigation information, but will not be as instinctive from a "driving" perspective.

To illustrate: if the operator wishes to insert the catheter tip toward the targeted tissue site 150 watching only the rightmost view 144 without the master input device 12 coordinate system synchronized with such view, the operator would have to remember that pushing straight ahead on the master input device will make the distal tip representation 148 move to the right on the rightmost display 144. Should the operator decide to toggle the system to use the rightmost view 144 as the primary navigation view, the coordinate system of the master input device 12 is then synchronized with that of the rightmost view 144, enabling the operator to move the catheter tip 148 closer to the desired targeted tissue location 150 by manipulating the master input device 12 down and to the right. The synchronization of coordinate systems may be conducted using fairly conventional mathematic relationships which are described in detail in the aforementioned applications incorporated by reference.

Referring back to embodiment of FIG. 13, the master computer 126 also comprises software and hardware interfaces to operator control station buttons, switches, and other input devices which may be utilized, for example, to "freeze" the system by functionally disengaging the master input device as a controls input, or provide toggling between various scaling ratios desired by the operator for manipulated inputs at the master input device 12. The master computer 126 has two separate functional connections with the control and instrument driver computer 128: one connection 132 for passing controls and visualization related commands, such as desired XYZ (in the catheter coordinate system) commands, and one connection 134 for passing safety signal commands. Similarly, the control and instrument driver computer 128 has two separate functional connections with the instrument and instrument driver hardware 130: one connection 136 for passing control and visualization related commands such as required-torque-related voltages to the amplifiers to drive the motors and encoders, and one connection 138 for passing safety signal commands. Also shown in the signal flow overview of FIG.

13 is a pathway 140 between the physical instrument and instrument driver hardware 130 back to the master computer 126 to depict a closed loop system embodiment wherein instrument localization technology is utilized to determine the actual position of the instrument to minimize navigation and control error.

II. Tension Sensing.

Figure 15:
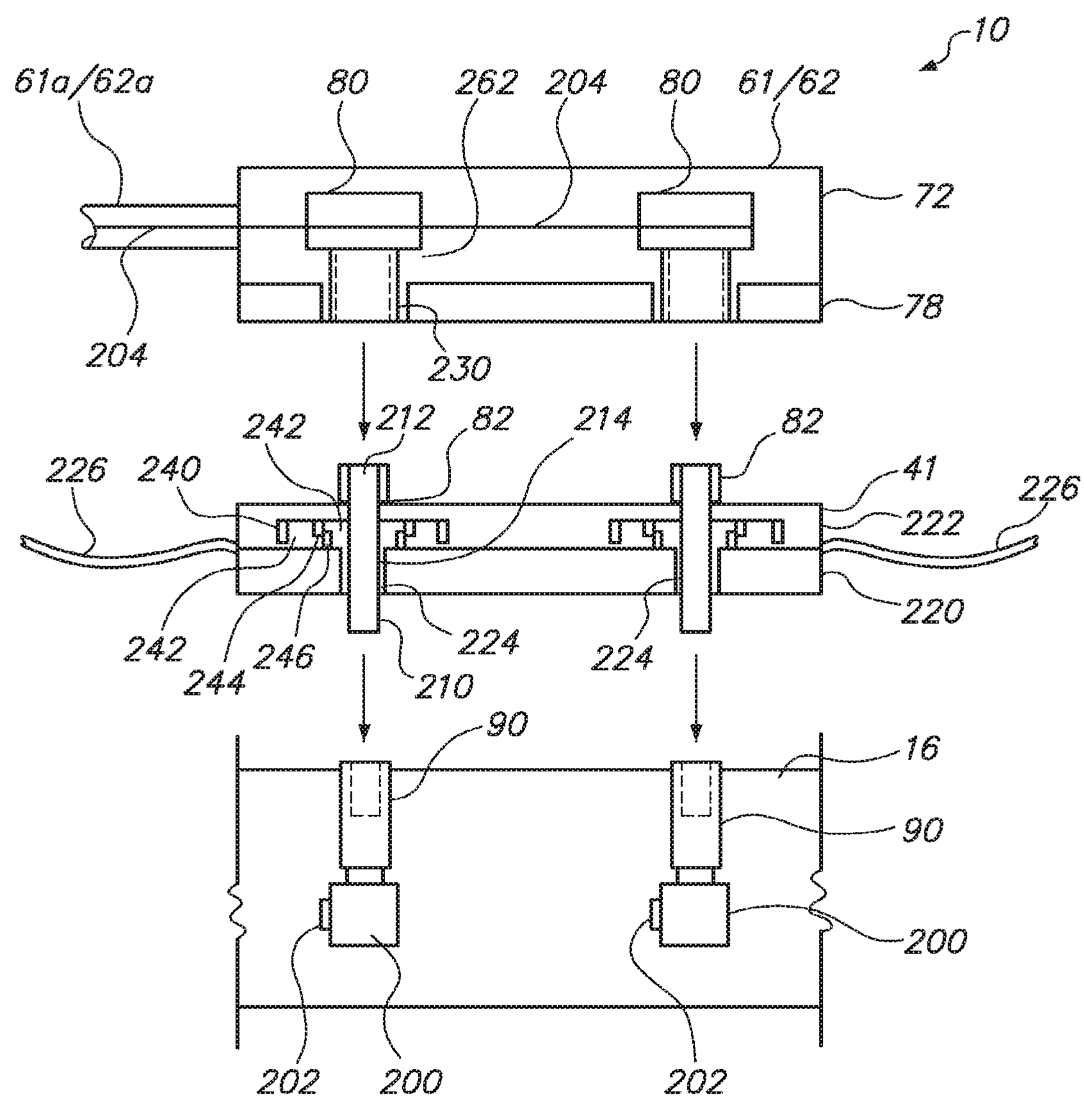
FIG. 15 illustrates some components of a robotic system that includes tension sensing capability in accordance with some embodiments.

As discussed with reference to FIGS. 6-7, the robotic system 10 includes an instrument driver (or drive assembly) 16 with sleeve receptacles 90 for turning the respective shafts 82 at the sterile adaptor 41, which in turn, rotates the respective pulley assemblies 80 at the splayer 61/62. In some embodiments, the robotic system 10 may further include a sensor for sensing a characteristic that corresponds with an amount of force or torque being applied to turn the sleeve receptacles 90. FIG. 15 illustrates some components of the robotic system 10 that includes tension sensing capability in accordance with some embodiments. As shown in the figure, the instrument driver 16 includes the sleeve receptacles 90, which are actuatable elements that are actuated by respective motors 200. The instrument driver 16 also includes sensors 202 coupled to the respective motors 200. Each sensor 202 is configured to sense a characteristic that corresponds with an amount of force or torque being applied to the actuatable element 90. The sensor 202 is illustrated schematically as being coupled to the motor 200. In some embodiments, the sensor 202 may be located internally inside a motor. In other embodiments, the sensor 202 may be secured to an exterior of a motor. In other embodiments, the sensor 202 may be attached to a component that is coupled to the motor. For example, in some embodiments, the motor 200 may be mounted to a ring structure (like the ring structure 300 shown in FIG. 19) that is attached to the instrument driver 16. In such cases, the sensor 202 may be attached to the ring structure, and the sensor 202 may be considered as being coupled to the motor 200 (indirectly, in this example).

The robotic system 10 also includes the sterile adaptor 41, which has a base 220 with a plurality of openings 224 for housing respective rotary members 82. In the illustrated embodiments, the rotary members 82 are shafts configured for detachably coupling to respective sleeve receptacles 90. In particular, each rotary member 82 has a first end 210 for insertion into the sleeve receptacle 90, a second end 212, and a body 214 extending between the first and second ends 210, 212. The sterile adaptor 41 also includes a cover 222 that is coupled to the base 220, and a flexible sheet (membrane) 226 for providing a sterile barrier so that after the splayer assembly 61/62 is used, the sterile adaptor 41 and the splayer assembly 61/62 may be discarded, while leaving the instrument driver 16 sterile.

The robotic system 10 also includes the splayer 61/62, which includes a base 78 with a plurality of openings 230 for housing respective pulley assemblies 80, and a cover 72 for coupling to the base 78. When the cover 72 is coupled to the base 78, it covers the pulley assemblies 80. The splayer 61/62 also includes an elongate member 61*a*/62*a* coupled to the base 78 (e.g., either directly to the base 78, or indirectly to the base 78 through the cover 72). The elongate member 61*a*/62*a* may be a catheter, a sheath, or any elongate instrument having a lumen extending therethrough. The robotic system 10 also includes a plurality of steering wires 204 disposed in the elongate member 61*a*/62*a*. Each steering wire 204 has a distal end coupled to a distal end of the elongate member, and a proximal end coupled to one of the pulley assemblies 80. During use, the pulley assembly may be rotated to apply tension to the steering wire 204 to thereby apply tension to the steering wire 204, which in turn, causes the distal end of the elongate member 61*a*/62*a* to bend. Although two pulley assemblies 80 are shown, it should be understood that in other embodiments, the splayer 61/62 may have more than two pulley assemblies 80 (e.g., four pulley assemblies 80), with respective steering wires 204 connected thereto. Also, in other embodiments, the splayer 61/62 may have only one pulley assembly 80, and the elongate member 61*a*/62*a* may have only one steering wire 204 connected to the pulley assembly 80.

As shown in the figure, the actuatable element 90 is configured to turn the pulley assembly 80 indirectly through the rotary member 82 at the sterile adaptor 41 to thereby apply tension to the steering wire 204 at the catheter 61*a*/sheath 62*a*. The sensor 202 is configured to sense a characteristic that corresponds with an amount of force being applied to the actuatable element 90. By means of non-limiting examples, the characteristic may be an actual force, a torque (which is force times distance), a strain, a stress, an acceleration, etc. The sensed characteristic may be used to correlate an amount of tension being applied to the steering wire 204. In some embodiments, the sensed characteristic may be transmitted from the sensor 202 to the user interface 2, and the value of the sensed characteristic may be displayed on a screen for presentation to a user. Also, in some embodiments, the sensed characteristic may be transmitted from the sensor 202 in a form of a signal to a processor, which processes the signal, and controls an amount of torque/force being applied to the motor 200 in response to the processed signal.

In some embodiments, in order to accurately correlate the sensed characteristic by the sensor 202 with an amount of tension being applied at the steering wire 204, it may be desirable to minimize, or at least reduce an amount of friction between the shaft 82 and the base 220 at the sterile adaptor 41. In the illustrated embodiments, the sterile adaptor 41 includes an interface between each rotary member 82 and the base 220 for reducing an amount of friction therebetween (i.e., between the shaft body 214 of the rotary member 82 and the wall in the opening 224 defined by the base 220). As shown in the figure, each rotary member 82 includes a flange 240 disposed circumferentially around the shaft body 214, and a plurality of slots 242 at the flange 240. Two slots 242 are shown, which are defined by a partition 244 extending round the shaft body 214 of the rotary member 82. The partition 244 may have a ring configuration. For example, the partition 244 may have a continuous ring structure, or alternatively, a plurality of structures that form a ring configuration. Each slot 242 has a ring configuration that extends around the shaft body 214 of the rotary member 82. Also, as shown in the figure, the base 220 includes a protrusion 246 next to (e.g., within 5 cm or less from) the opening 224. The protrusion 246 has a ring configuration around the opening 224, and extends into a slot 242. For example, the protrusion 246 may have a continuous ring structure, or alternatively, may have a plurality of structures that form into a ring configuration. Although one protrusion 246 is shown in the example, in other embodiments, the sterile adaptor 41 may include a plurality of protrusions 246 that extend into respective ones of the slots 242 at the flange 240. Also, in other embodiments, the flange 240 of the rotary member 82 may include more than two slots 242, or less than two slots 242 (e.g., only one slot 242).

In the illustrated embodiments, the cross sectional dimension of the shaft body 214 is less than the cross sectional dimension of the opening 224 (e.g., by 3 mm, and more preferably by 2 mm, and even more preferably by 1 mm or less). The partition(s) 244 at the flange 240 and the protrusion(s) 246 at the base 220 cooperate with each other (e.g., engage with each other) to prevent the shaft 214 from touching the surrounding wall at the opening 224. Accordingly, the shaft body 214 essentially "floats" within the space defined by the opening 224. In the illustrated embodiments, the partition 244 abuts against the protrusion 246 while the shaft body 214 is maintained within the opening 224 so that it is spaced away from the wall of the opening 224. In other embodiments, the partition 244 may not abut against the protrusion 246. Instead, there may be a small gap between the partition 244 and the protrusion 246 to reduce friction between the partition 244 and the protrusion 246. The gap may be large enough to allow some movement of the shaft body 214 relative to the base 220, while small enough to prevent the shaft body 214 from touching the wall at the opening 224.

In some embodiments, to further provide a frictionless interface, the partition(s) 244 and/or the protrusion(s) 246 may be coated with a hydrophobic material to allow fluid to glide easily along the surfaces of these components. Also, in some embodiments, a lubricant, such as oil, may be applied to the surface of the partition(s) 244 and/or the protrusion(s) 246.

During use, the sterile adaptor 41 is detachably coupled to the instrument driver 16. Such may be accomplished by inserting the first ends 210 of the respective rotary members 82 into respective openings at the acutatable elements 90 (like that shown in FIG. 7E). The membrane 226 provides a barrier to prevent the instrument driver 16 from being contaminated during a medical procedure. Also, during use, the splayer 61 is detachably coupled to the sterile adaptor 41. Such may be accomplished by inserting the second ends 212 of the respective rotary members 82 into respective openings at the end of the rotary members 80 (like that shown in FIG. 7D).

The same setup may be performed for the splayer 62. In particular, during use, another sterile adaptor 41 is detachably coupled to the instrument driver 16. Such may be accomplished by inserting the first ends 210 of the respective rotary members 82 into respective openings at the acutatable elements 90 (like that shown in FIG. 7E). Also, the splayer 62 is detachably coupled to the sterile adaptor 41. Such may be accomplished by inserting the second ends 212 of the respective rotary members 82 into respective openings at the end of the rotary members 80 (like that shown in FIG. 7D).

After the splayers 61, 62 are mounted to respective sterile adaptors 41, and after the sterile adaptors 41 are mounted to the instrument driver 16, the robotic system 10 may then be used to perform a medical procedure. For example, in some embodiments, the splayer 61 and/or splayer 62 may be controlled to position the catheter 61*a* and/or the sheath 62*a* at desired position(s) within the patient. Once the catheter 61*a* and/or the sheath 62*a* have been desirably positioned, the catheter 61*a* and/or the sheath 62*a* may then be used to deliver an instrument (e.g., an ablation device) or a substance (e.g., occlusive device, drug, etc.) to treat the patient.

Various techniques may be employed to move the catheter 61*a* and/or the sheath 62*a* to thereby place these instruments at desired positions(s) in the patient. In some embodiments, the instrument driver 16 may be configured to translate the splayer 61 to thereby translate the catheter 61*a* in an axial direction. Also, the instrument driver 16 may be configured to translate the splayer 62 to thereby translate the sheath 62*a* in an axial direction. Thus, by moving the splayer 61 and/or splayer 62, the instrument driver 16 may advance or retract the catheter 61*a* relative to the sheath 62*a*, and vice versa. Also, if the movements of the splayers 61, 62 are synchronized, both the catheter 61*a* and the sheath 62*a* may be moved by the same amount in some embodiments. In some embodiments, the translation of the splayer 61 and/or the splayer 62 may be performed by the instrument driver 16 in response to a command signal received from the user interface. For example, in some embodiments, the instrument driver 16 may be configured to receive a command signal input from a user at the user interface, and generate a control signal in response to the command signal to move one or both of the splayers 61, 62.

Also, in some embodiments, the instrument driver 16 may be configured to bend a distal end of the catheter 61*a*, a distal end of the sheath 62*a*, or both. For example, in some embodiments, the instrument driver 16 may actuate one or more motors at the instrument driver 16 to turn one or more respective actuatable elements 90, thereby turning one or more respective rotary members 80 at the splayer 61 indirectly through the one or more respective rotary members 82 at the sterile adaptor 41. The turning of the one or more rotary members 80 at the splayer 61 applies tension to one or more respective steering wires to thereby bend the catheter 61*a* towards a certain direction.

Similarly, in some embodiments, the instrument driver 16 may actuate one or more motors at the instrument driver 16 to turn one or more respective actuatable elements 90, thereby turning one or more respective rotary members 80 at the splayer 62 indirectly through the one or more respective rotary members 82 at the sterile adaptor 41. The turning of the one or more rotary members 80 at the splayer 62 applies tension to one or more respective steering wires to thereby bend the sheath 62*a* towards a certain direction.

In some embodiments, as the rotary member 80 is being turned to apply tension to the steering wire 204, the sensor 202 senses a characteristic that correlates with an amount of force or torque being applied by the actuatable element 90. For example, in some embodiments, the sensor 202 may be a torque sensor configured to measure an amount of torque being applied to the actuatable element 90. The measured torque may be divided by a moment arm (e.g., a radius of the actuatable element 90) to derive a force value. In some embodiments, the force value may correlate with an amount of tension being applied to the steering wire 204. For example, in some cases, the force value may be considered to be the amount of tension being applied to the steering wire 204. In other embodiments, the sensor 202 may be a force sensor configured to measure a force vector that is in opposite direction as the tension force at the steering wire 204. Because of the frictionless interface at the sterile adaptor 41, the force sensed by the sensor 202 may be substantially equal to (e.g., at least 80%, and more preferably at least 90%, and even more preferably at least 99% of) the amount of tension at the steering wire 204.

In some embodiments, the sensed characteristic by the sensor 202 may be used in a process to steer the distal end of the catheter 61*a*/sheath 62*a* so that the distal end achieves a desired amount of bending. For example, in some embodiments, in a method of steering the distal end of the catheter 61*a*/sheath 62*a* (elongate member), an amount of bending to be achieved by the distal end of the elongate member may first be determined. Such may be accomplished by a user of the system 10. Alternatively, such may be accomplished automatically by a processor based on an anatomy of the patient, and the location of the elongate member 61*a*/62*a*. Next, an amount of tension to be applied to the steering wire 204 located within the elongate member 61*a*/62*a* may be determined based on the amount of bending that is desired to be achieved. In general, the more tension is being applied to the steering wire 204, the more the amount of bending will be achieved at the distal end of the elongate member 61*a*/62*a*. In some embodiments, the amount of tension may be calculated automatically by the processor based on structural properties (e.g., bending stiffness) of the elongate member 61*a*/62*a*. Next, the instrument driver 16 actuates the actuatable element 90 to apply a torque to turn the rotary member 80 that is detachably coupled (directly or indirectly through element 82) to the actuatable element 90. The application of the torque by the actuatable element 90 causes tension to be applied to the steering wire 204. While the actuatable element 90 is being actuated, the sensor 202 senses a characteristic that corresponds with an amount of force or torque being applied by the actuatable element 90 to turn the rotary member 80. In the illustrated embodiments, the act of using the actuatable element 90 to apply the torque comprises increasing the amount of force or torque being applied by the actuatable element 90 until the sensed characteristic by the sensor 202 indicates that the determined amount of tension at the steering wire 204 has been achieved. The above technique for bending the elongate member 61*a*/62*a* is advantageous because it obviates the need to determine how much axial movement (e.g., due to axial strain of the steering wire 204, and relative movement between the steering wire 204 and the elongate member 61*a*/62*a*) needs to be achieved by the steering wire 204 in order to achieve a certain desired amount of bending. In particular, the above technique involving use of the sensor 202 is advantageous over another technique of achieving a desired amount of bending, which involve determining how much tension is needed at the steering wire 204, and then determining a required amount of axial movement by the steering wire 204 that corresponds with the determined tension. Then the system monitors an amount of axial movement by the steering wire 204 until the required amount of axial movement by the steering wire 204 is achieved. However, calculating the required amount of axial movement needs to be achieved by the steering wire based on the required tension may be difficult, computational intensive, and may not be accurate.

Also as illustrated in the above embodiments, the frictionless interface at the sterile adaptor 41 is advantageous because it significantly remove all or most of the friction between the rotary member 82 and its surrounding wall in the opening 224. Thus, the frictionless interface at the sterile adaptor 41 is preferred over rubber seal, and the robotic system 10 does not include any rubber seal between the rotary member 82 and the base 220 of the sterile adaptor 41.

Figures 16, 17, 18:
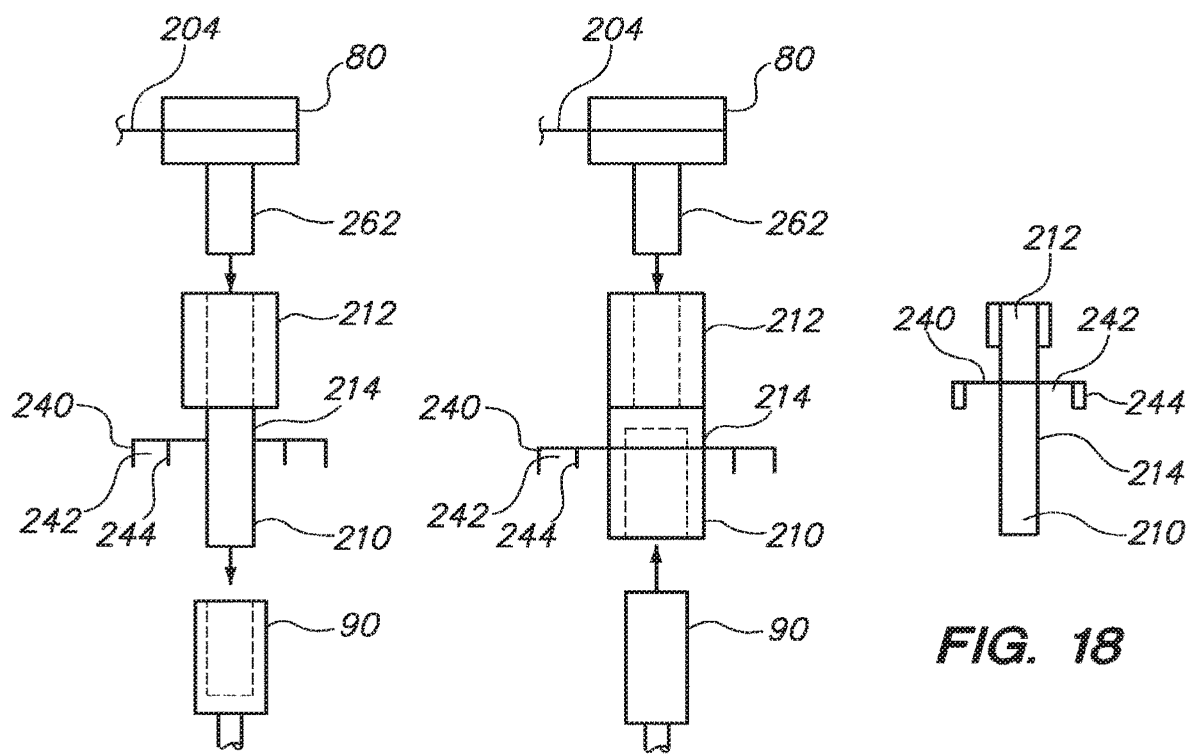
FIG. 16 illustrates some components of a robotic system that includes tension sensing capability in accordance with other embodiments.
FIG. 17 illustrates some components of a robotic system that includes tension sensing capability in accordance with other embodiments.
FIG. 18 illustrates a frictionless interface at a sterile adaptor in accordance with some embodiments.

In the above embodiments, the rotary member 80 at the splayer 61/62 has been described as having an opening at one end of the rotary member 80 for receiving the second end 212 of the rotary member 82 at the sterile adaptor 41. In other embodiments, the configuration of the coupling may be reversed. For example, in other embodiments, the rotary member 80 at the splayer 61/62 may have an end for insertion into an opening at the second end 212 of the rotary member 82 at the sterile adaptor 41 (FIG. 16).

Also, in the above embodiments, the first end 210 of the rotary member 82 at the sterile adaptor 41 has been described as being inserted into an opening at the actuatable element 90 at the instrument driver 16. In other embodiments, the configuration of the coupling may be reversed. For example, in other embodiments, the first end 210 of the rotary member 82 at the sterile adaptor 41 may have an opening for receiving an end of the actuatable element 90 at the instrument driver 16 (FIG. 17). Furthermore, in other embodiments, the second end 212 of the rotary member 82 in the embodiments of FIG. 17 may be configured for insertion into an opening at the end of the rotary member 80 (like that shown in FIG. 15).

In the above embodiments, the frictionless interface at the sterile adaptor 41 includes two slots 242 and a protrusion 246 inserted into one of the slots 242. In other embodiments, the frictionless interface may include an additional protrusion 246 extending into the second slot 242. Also, in further embodiments, the frictionless interface may include only one slot 242 (FIG. 18).

As discussed, the sensor 202 is coupled to the motor 200, either directly or indirectly. Various techniques may be employed for coupling the sensor 202 to the motor 200. In some embodiments, the sensor 202 may be a strain gauge mounted to an output shaft. In other embodiments, the sensor 202 may be a torque sensor mounted in series with the output shaft.

Figure 19:
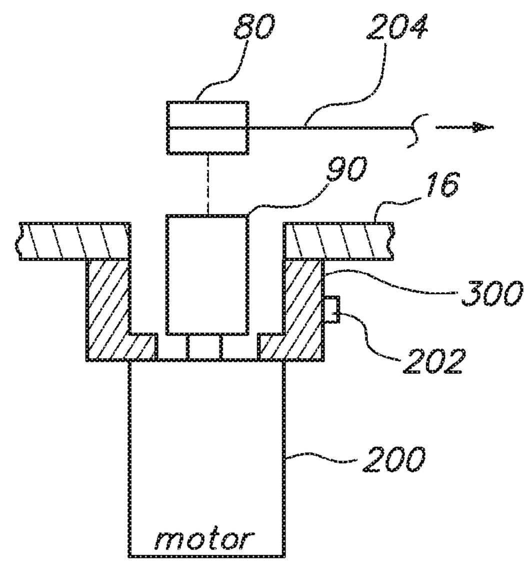
FIG. 19 illustrates some components of a robotic system that includes tension sensing capability in accordance with other embodiments.

In further embodiments, the motor 200 (with optional gearbox) may be mounted to the instrument driver 16 (e.g., to a chassis of the instrument driver) through a mounting structure 300 (FIG. 19). In such cases, the sensor 202 may be attached to the mounting structure 300. Such configuration is advantageous because it allows torque to be measured at the output shaft by measuring the reaction forces from the entire gear train. This is because at static equilibrium, the measured reaction torque may be equal to the output shaft torque. The mounting structure 300 has a ring configuration in some embodiments. In other embodiments, the mounting structure 300 may have other configurations. Also, in some embodiments, the mounting structure 300 may be considered to be a part of the sensor 202. The sensor 202 (and optionally with the mounting structure 300) may be a torque sensor, a hinge or flexure based structure with integrated load cell(s) or strain gauge(s), or a strain gauge mounted to an otherwise rigid mounting structure.

In some cases, the sensor 202 may pick up inertial forces from the acceleration and deceleration of the motor 200. Options for minimizing this contamination include (1) low-pass filtering the measured signal, (2) using only data collected when the motor 200 is stationary or moving at an approximately constant velocity, and/or (3) modeling the inertial effects of the motor 200, and compensating the measured signal based upon a measured acceleration by an encoder at the motor 200 and/or motor back-EMF.

Figure 20:
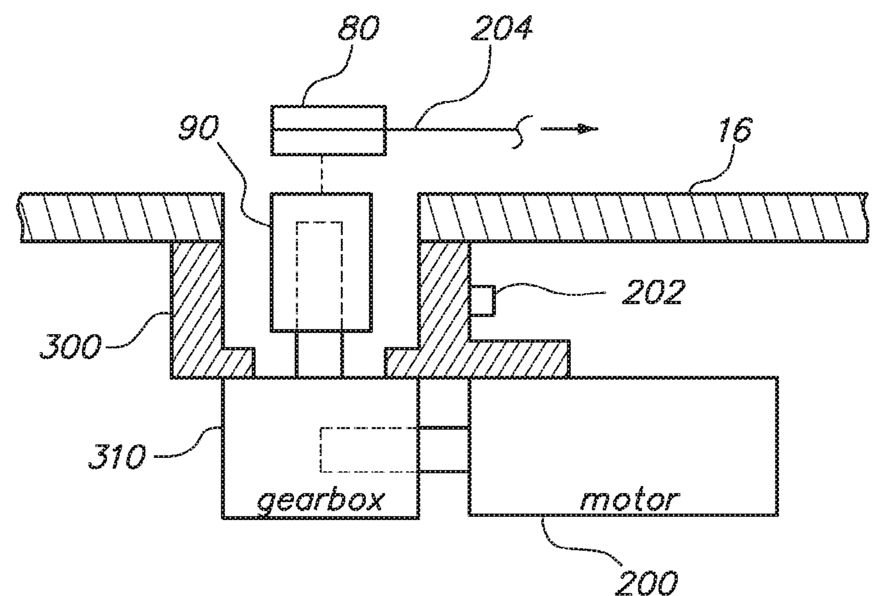
FIG. 20 illustrates some components of a robotic system that includes tension sensing capability in accordance with other embodiments.

In other embodiments, by mounting the axis of the motor 200 at 90° relative to the axis of the output shaft, the inertia forces due to acceleration and deceleration of the motor 200 will be decoupled from the measured reaction torque (FIG. 20). As shown in the figure the robotic system 10 may optionally further include a gear box 310 for transmitting torque from the motor 200 to the output shaft that is axially aligned with the actuatable element 90. In such cases, the acceleration of the output shaft, pulley, etc., may still contaminate the measurement of wire tension, but these contributions will be relatively small compared to the acceleration of the motor rotor, especially because of the effects of gear reduction between motor and output shaft. The sensor 202 (and optionally with the mounting structure 300) may be a torque sensor, a hinge or flexure based structure with integrated load cell(s) or strain gauge(s), or a strain gauge mounted to an otherwise rigid mounting structure.

Figure 21:
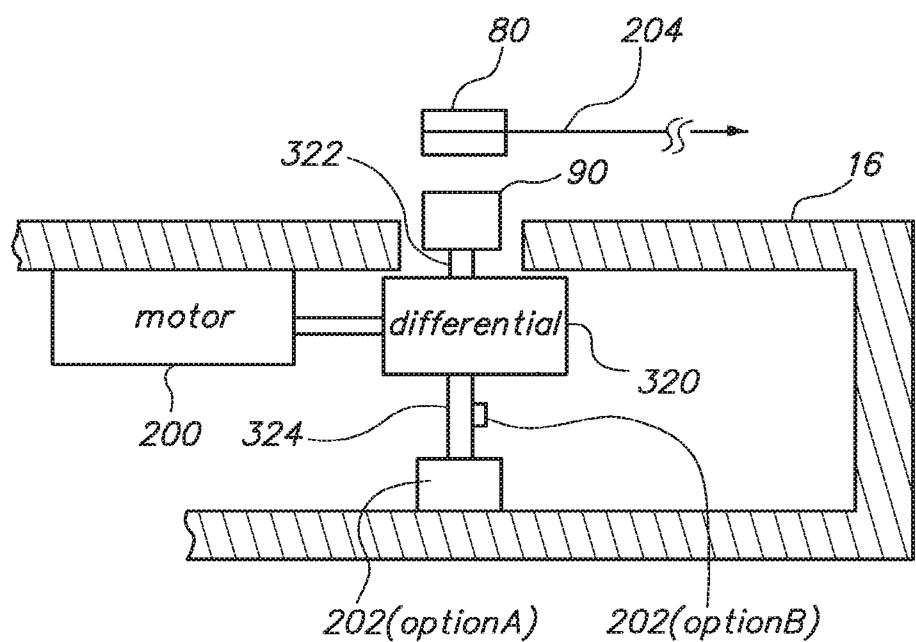
FIG. 21 illustrates some components of a robotic system that includes tension sensing capability in accordance with other embodiments.

In further embodiments, the instrument driver 16 may include a differential gearbox 320 mechanically coupled to the motor 200 (FIG. 21). The gearbox 320 is configured to turn a first output shaft 322 that is coupled to the actuatable element 90, while a second output shaft 324 extending from the gearbox 320 is fixed to the instrument driver 16 (e.g., to a chassis of the instrument driver 16). In some embodiments, the second output shaft 324 may be fixed to the instrument driver 16 through the sensor 202 (see option A in figure), which may be a torque sensing element in some embodiments. Alternatively, the second output shaft 324 may be fixed to the instrument driver 16 without using the sensor 202, in which cases, the sensor 202 (which may be a strain gauge in some embodiments) may be secured to the second output shaft 324 (see option B in figure). The gearbox 320 is advantageous because it allows the sensor 202 to be coupled to a component that experiences torque from the gearbox 320, but does not spin (which is beneficial because it obviates the need to implement complicated signal connection, such as a slip connection, that may otherwise be needed if the sensor 202 is coupled to a spinning shaft). In some embodiments, the gearbox 320 may be similar to that used in transferring power to both wheels of an automobile while allowing them to rotate at different speeds. In some cases, the difference between the torque in the upper and lower output shafts 322, 324 may be due to inefficiencies of the differential gearbox 320. In such cases, by maximizing the efficiency of the differential gearbox 320, the sensor 202 may provide a good estimate of the pullwire tension without having to deal with routing signal connections to a sensor that is moving. Also, in some embodiments, the configuration of the embodiments shown in FIG. 21 may be simplified by incorporating the secondary (fixed) output shaft 324 and the sensor 202 entirely within a housing of the differential gearbox 320. This may provide for a compact gearbox with integrated output shaft torque sensing and no limitations on output shaft motion.

III. Driving Modes

As discussed, the system 10 may be configured to move the sheath 62*a* distally or proximally, move the catheter 61*a* distally or proximally, and to move the elongate member 26 distally or proximally. In some cases, the movement of the sheath 62*a* may be relative to the catheter 61*a*, while the catheter 61*a* remains stationary. In other cases, the movement of the catheter 61*a* may be relative to the sheath 62*a* while the sheath 62*a* remains stationary. Also, in other cases, the sheath 62*a* and the catheter 61*a* may be moved together as a unit. The elongate member 26 may be moved relative to the sheath 62*a* and/or the catheter 61*a*. Alternatively, the elongate member 26 may be moved together with the sheath 62*a* and/or the catheter 61*a*.

In some embodiments, the workstation 2 is configured to provide some or all of the following commanded motions (driving modes) for allowing the physician to choose. In some embodiments, each of the driving modes may have a corresponding button at the workstation 2 and/or the bedside control 402.

Elongate member Insert—When this button/command is selected, the manipulator 24 inserts the elongate member 26 at a constant velocity.

Elongate member Roll—When this button/command is selected, the manipulator 24 rolls the elongate member 26 at a constant angular velocity Elongate member Size—When the size or gauge of the elongate member 26 is inputted into through the user interface, the system will automatically alter roll and insert actuation at the proximal end of the elongate member 26 accordingly to achieve desired commanded results. In one implementation, when a user inputs the elongate member's size, the system automatically changes its kinematic model for driving that elongate member 26. So if the user commands the elongate member 26 to move to a certain position, the system will calculate, based on the kinematic model, roll and insert commands, which may be different for different elongate member sizes (e.g., elongate members 26 with different diameters). By inputting the elongate member's size, the system knows which kinematic model to use to perform the calculation. Such feature is beneficial because different sized elongate members 26 behave differently.

Leader/Sheath Select—When this button/command is selected, it allows the user to select which device (e.g., catheter 61*a*, sheath 62*a*, elongate member 26, or any combination of the foregoing) is active.

Leader/Sheath Insert/Retract—When this button/command is selected, the instrument driver assembly inserts or retracts the catheter 61*a*/sheath 62*a* while holding the elongate member 26 and any non-active device fixed relative to the patient. When this motion causes the protruding section of the catheter 61*a* to approach zero (due to insertion of the sheath 62*a* or retraction of the catheter 61*a*), the system automatically relaxes the catheter 61*a* as part of the motion.

Leader/Sheath Bend—When this button/command is selected, the instrument driver assembly bends the articulating portion of the catheter 61*a*/sheath 62*a* within its currently commanded articulation plane.

Leader/Sheath Roll—When this button/command is selected, the instrument driver assembly uses the pullwires to "sweep" the articulation plane of the device (catheter 61*a* and/or sheath 62*a*) around in a circle through bending action of the device. Thus, this mode of operation does not result in a true "roll" of the device in that the shaft of the device does not roll. In other embodiments, the shaft of the device may be configured to rotate to result in a true roll. Thus, as used in this specification, the term "roll" may refer to an artificial roll created by seeping a bent section, or may refer to a true roll created by rotating the device.

Leader/Sheath Relax—When this button/command is selected, the instrument driver assembly gradually releases tension off of the pullwires on the catheter 61*a*/sheath 62*a*. If in free space, this results in the device returning to a straight configuration. If constrained in an anatomy, this results in relaxing the device such that it can most easily conform to the anatomy.

Elongate Member Lock—When this button/command is selected, the elongate member 26 position is locked to the catheter 61*a* position. As the leader is articulated or inserted, the elongate member 26 moves with the catheter 61*a* as one unit.

System Advance/Retract—When this button/command is selected, the instrument driver assembly advances/retracts the catheter 61*a* and sheath 62*a* together as one unit. The elongate member 26 is controlled to remain fixed relative to the patient.

Autoretract—When this button/command is selected, the instrument driver assembly starts by relaxing and retracting the catheter 61*a* into the sheath 62*a*, and then continues by relaxing and retracting the sheath 62*a* with the catheter 61*a* inside it. The elongate member 26 is controlled to remain fixed relative to the patient.

Initialize Catheter—When this button/command is selected, the system confirms that the catheter 61*a* and/or the sheath 62*a* has been properly installed on the instrument driver assembly, and initiates pretensioning. Pretensioning is a process used to find offsets for each pullwire to account for manufacturing tolerances and the initial shape of the shaft of the catheter 61*a* and/or the sheath 62*a*.

Leader/Sheath Re-calibration—When this button/command is selected, the instrument driver assembly re-pretensions the catheter 61*a* and/or the sheath 62*a* in its current position. This gives the system the opportunity to find new pretension offsets for each pullwire and can improve catheter driving in situations where the proximal shaft of the catheter 61*a* has been placed into a significant bend. It is activated by holding a relax button down for several seconds which ensures that the device is fully de-articulated. Alternatively the re-calibration may be activated without holding down the relax button to de-articulate the device.

Leader Relax Remove—When this button/command is selected, the instrument driver assembly initiates a catheter removal sequence where the catheter 61*a* is fully retracted into the sheath 62*a*, all tension is released from the pullwires, and the splayer shafts (at the drivable assembly 61 and/or drivable assembly 62) are driven back to their original install positions so that the catheter 61*a* can be reinstalled at a later time.

Leader Yank Remove—When this button/command is selected, the instrument driver assembly initiates a catheter removal sequence where the catheter 61*a* is removed manually.

Emergency Stop—When this button/command is selected, the instrument driver assembly initiates a gradual (e.g., 3 second) relaxation of both the catheter 61*a* and the sheath 62*a*. The components (e.g., amplifier) for operating the catheter 61*a*, elongate member 26, or another device are placed into a "safe-idle" mode which guarantees that no power is available to the motors that drive these elements, thereby bringing them rapidly to a stop, and allowing them to be manually back-driven by the user. Upon release of the emergency stop button, the system ensures that the catheter 61*a* is still in its allowable workspace and then returns to a normal driving state.

Figure 22A:
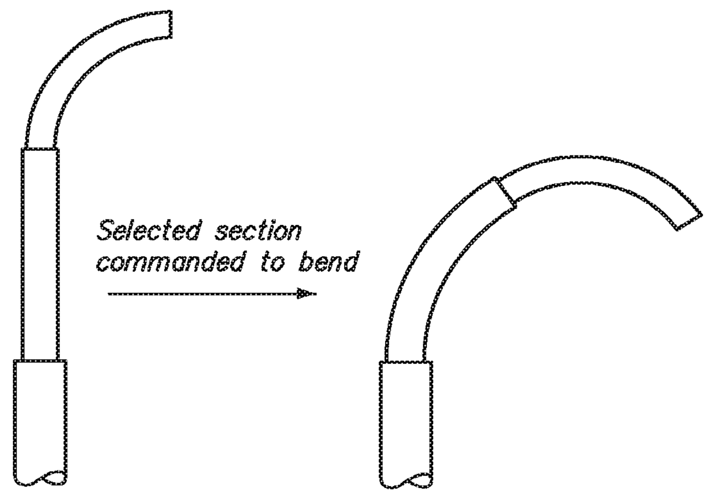
FIG. 22A illustrates driving mode(s) in accordance with some embodiments.

Segment control: In some embodiments, the workstation 2 allows a user to select individual segment(s) of a multi-segment catheters (such as the combination of the catheter 61*a* and the sheath 62*a*), and control each one. The advantage of controlling the catheter in this way is that it allows for many options of how to control the movement of the catheter, which may result in the most desirable catheter performance. To execute this method of catheter steering, the user selects a segment of the catheter to control. Each segment may be telescoping or non-telescoping. The user may then control the selected segment by bending and inserting it using the workstation 2 to control the position of the end point of the catheter. Other segment(s) of the catheter will either maintain their previous position (if it is proximal of the selected section) or maintain its previous configuration with respect to the selected section (if it is distal of that section) (FIG. 22A).

Figure 22B:
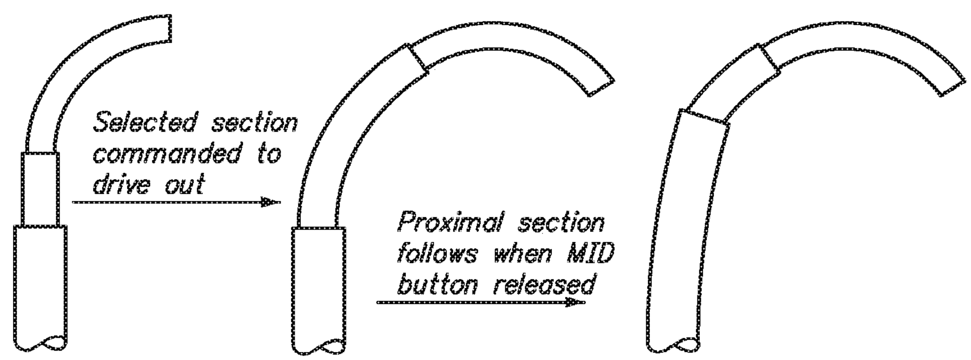
FIG. 22B illustrates driving mode(s) in accordance with other embodiments.

Follow mode: In some embodiments, the workstation 2 allows the user to control any telescoping section while the more proximal section(s) follows behind automatically. This has the advantage of allowing the user to focus mostly on the movement of a section of interest while it remains supported proximally. To execute this method of catheter steering, the user first selects a telescoping section of the elongate instrument (e.g., catheter 61*a* and sheath 62*a*) to control. This section is then controlled using the workstation 2 to prescribe a location of the endpoint of the segment. Any segment(s) distal of the section of interest will maintain their previous configuration with respect to that section. When the button on the workstation 2 is released, any segment(s) proximal of the section of interest will follow the path of the selected section as closely as possible until a predefined amount of the selected section remains (FIG. 22B). As an alternative to this driving mode, the segment(s) of the elongate instrument which is proximal of the section of interest could follow along as that segment is moved instead of waiting for the button to be released. Furthermore, with either of these automatic follow options, the system may optionally be configured to re-pretension the sections that have been driven out and re-align the sections that are proximal of the driven section.

Figure 22C:
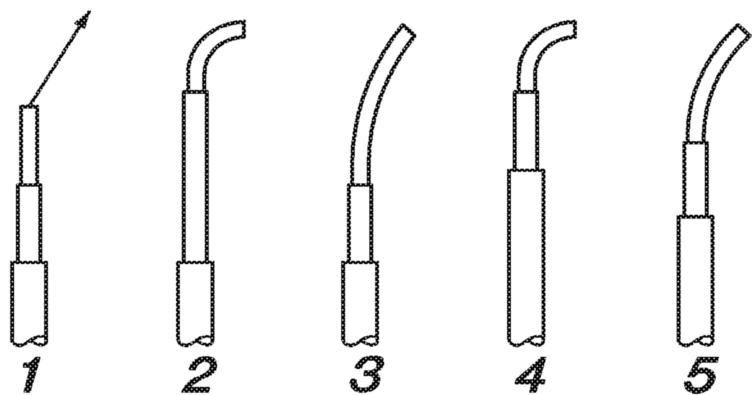
FIG. 22C illustrates driving mode(s) in accordance with other embodiments.
Figure 22D:
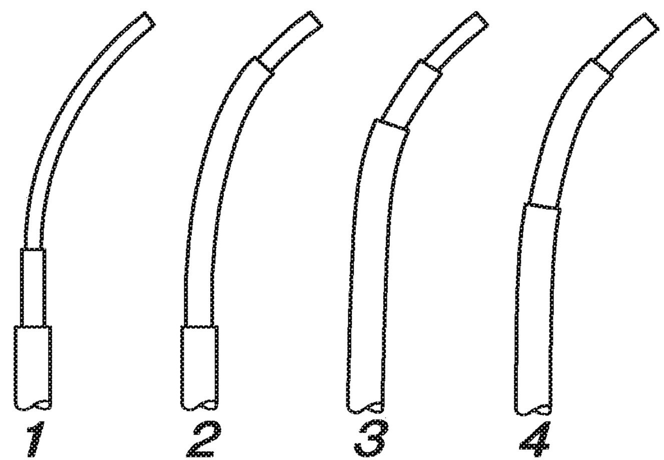
FIG. 22D illustrates driving mode(s) in accordance with other embodiments.

Follow mode may be desirable to use to bring the more proximal segments of the elongate instrument towards the tip to provide additional support to the distal segment. In cases where there are three or more controllable sections of the elongate instrument, there are several options for how to execute a "follow" command. Consider the example in FIG. 22D where the distal segment (which may be a guidewire or a steerable instrument in some embodiments) has been driven out as shown in frame 1. The "follow" command could be executed by articulating and/or inserting only the middle segment (which may be the catheter 61*a* in some embodiments) of the elongate instrument as shown in frame 2. The "follow" command could be executed by articulating and/or inserting only the most proximal segment (which may be the sheath 62*a* in some embodiments) of the elongate instrument as shown in frame 3. The "follow" command could also be executed by coordinating the articulation and/or insertion of multiple proximal segments of the elongate instrument as shown in frame 4. Combining the motion of multiple sections has several potential advantages. First, it increases the total degrees-of-freedom available to the algorithm that tries to fit the shape of the following section(s) to the existing shape of the segment being followed. Also, in comparison to following each segment sequentially, a multi-segment follow mode simplifies and/or speeds up the workflow. In addition, multi-segment increases the distance that can be followed compared to when only one proximal segment is used to follow the distal segment.

Mix-and-match mode: In some embodiments, the workstation 2 allows the user to have the option of mixing and matching between articulating and inserting various sections of a catheter. For example, consider the illustration in FIG. 22C, and assuming that the distal most section of the elongate instrument is the "active" segment. If the user commands a motion of the tip of the elongate instrument as indicated by the arrow in Frame 1, there are several options available for how to achieve this command: (1) Articulate and extend the "active" segment, which is illustrated in frame 3 and is likely considered the normal or expected behavior; (2) Articulate the active distal most segment and insert one of the other proximal segments, as illustrated in frames 2 and 4; (3) Articulate the active distal most segment and combine inserting motion of some or all of the segments, as illustrated in frame 5.

There are multiple potential reasons why the user might want to choose some of these options. First, by "borrowing" insert motion from other segments, some of the segments could be constructed with fixed lengths. This reduces the need for segments to telescope inside of each other, and therefore reduces the overall wall thickness. It also reduces the number of insertion degrees-of-freedom needed. Also, by combining the insert motion from several segments, the effective insert range-of-motion for an individual segment can be maximized. In a constrained space such as the vasculature, the operator may likely be interested in "steering" the most distal section while having as much effective insertion range as possible. It would simplify and speed up the workflow to not have to stop and follow with the other segments.

In other embodiments, the "follow" mode may be carried out using a robotic system that includes a flexible elongated member (e.g., a guidewire), a first member (e.g., the catheter 61*a*) disposed around the flexible elongated member, and a second member (e.g., the sheath 62*a*) disposed around the first member. The flexible elongated member may have a preformed (e.g., pre-bent) configuration. In some embodiments, the flexible elongated member may be positioned inside a body. Such may be accomplished using a drive mechanism that is configured to position (e.g., advance, retract, rotate, etc.) the flexible elongated member. In one example, the positioning of the flexible elongated member comprises advancing the flexible elongated member so that its distal end passes through an opening in the body.

Next, the first member is relaxed so that it has sufficient flexibility that will allow the first member to be guided by the flexible elongated member (that is relatively more rigid than the relaxed first member). In some embodiments, the relaxing of the first member may be accomplished by releasing tension in wires that are inside the first member, wherein the wires are configured to bend the first member or to maintain the first member in a bent configuration. After the first member is relaxed, the first member may then be advanced distally relative to the flexible elongated member. The flexible elongated member, while being flexible, has sufficient rigidity to guide the relaxed first member as the first member is advanced over it. The first member may be advanced until its distal end also passes through the opening in the body.

In some embodiments, the second member may also be relaxed so that it has sufficient flexibility that will allow the second member to be guided by the flexible elongated member (that is relatively more rigid than the relaxed second member), and/or by the first member. In some embodiments, the relaxing of the second member may be accomplished by releasing tension in wires that are inside the second member, wherein the wires are configured to bend the second member or to maintain the second member in a bent configuration. After the second member is relaxed, the second member may then be advanced distally relative to the flexible elongated member. The flexible elongated member, while being flexible, has sufficient rigidity to guide the relaxed second member as the second member is advanced over it. The second member may be advanced until its distal end also passes through the opening in the body. In other embodiments, instead of advancing the second member after the first member, both the first member and the second member may be advanced simultaneously (e.g., using a drive mechanism) so that they move together as a unit. In further embodiments, the acts of advancing the flexible elongated member, the first member, and the second member may be repeated until a distal end of the flexible elongated member, the first member, or the second member has passed through an opening in a body.

In the above embodiments, tension in pull wires in the second elongated member is released to make it more flexible than the first elongated member, and the second elongated member is then advanced over the first elongated member while allowing the first elongated member to guide the second elongated member. In other embodiments, the tension in the pull wires in the first elongated member may be released to make it more flexible than the second elongated member. In such cases, the more flexible first elongated member may then be advanced inside the more rigid second elongated member, thereby allowing the shape of the second elongated member to guide the advancement of the first elongated member. In either case, the more rigid elongated member may be locked into shape by maintaining the tension in the pull wires.

In some of the embodiments described herein, the flexible elongated member may be a guidewire, wherein the guidewire may have a circular cross section, or any of other cross-sectional shapes. Also, in other embodiments, the guidewire may have a tubular configuration. In still other embodiments, instead of a guidewire, the flexible elongated member may be the member 26. In further embodiments, the robotic system may further include a mechanism for controlling and/or maintaining the preformed configuration of the guidewire. In some embodiments, such mechanism may include one or more steering wires coupled to a distal end of the guidewire. In other embodiments, such mechanism may be the catheter 61*a*, the sheath 62*a*, or both. In particular, one or both of the catheter 61*a* and the sheath 62*a* may be stiffened (e.g., by applying tension to one or more wires inside the catheter 61*a* and/or the sheath 62*a*). The stiffened catheter 61*a* and/or the sheath 62*a* may then be used to provide support for the guidewire.

Also, in some of the embodiments described herein, any movement of the elongate member 26, the catheter 61*a*, and/or the sheath 62*a* may be accomplished robotically using a drive assembly. In some embodiments, the drive assembly is configured to receive a control signal from a processor, and actuate one or more driveable elements to move the elongate member 26, the catheter 61*a*, and/or the sheath 62*a*.

It should be noted that the driving modes for the system are not limited to the examples discussed, and that the system may provide other driving modes in other embodiments.

IV. Treatment Methods

FIGS. 23A-23F illustrate a method of treating tissue using the robotic system 10 in accordance with some embodiments. As an example, the method will be described with reference to treating liver tissue. However, it should be understood that the system 10 may be used to treat other types of tissue.

First, the robotic system 10 is setup by placing the catheter 61 into the lumen of the sheath 62, and by placing the elongate member 26 into the lumen of the catheter 61. Next, an incision is then made at a patient's skin, and the distal end of the catheter 61 is then inserted into the patient through the incision. In particular, the distal end of the catheter 61 is placed inside a vessel 2000 (e.g., a vein or an artery) of the patient. In some embodiments, the liver may be accessed from the femoral vein or femoral artery from either groin. In other embodiments, the liver may be accessed from the right sub-clavin in vein or the right jugular vein. In some embodiments, the initial insertion of the catheter 61 into the patient may be performed manually. In other embodiments, the initial insertion of the catheter 61 may be performed robotically using the system 10. In such cases, the user may enter a command at the workstation 2, which then generates a user signal in response thereto. The user signal is transmitted to a controller, which then generates a control signal in response to the user signal. The control signal is transmitted to the driver to drive the catheter 61 so that it advances distally into the patient. In some embodiments, while the catheter 61 is being inserted into the patient, the distal end 2300 of the elongate member 26 may be housed within the lumen of the catheter 61. In other embodiments, the distal end 2300 of the elongate member 26 may extend out of the lumen of the catheter 61 (which the flexible section 320 of the elongate member 26 is housed within the lumen of the catheter 61) as the catheter 61 is being inserted. In such cases, the sharp distal tip of the elongate member 26 may facilitate insertion through the patient's skin. In other embodiments, the tip of the elongate member 26 may not be sharp enough, or the distal section of the elongate member 26 may not be stiff enough, to puncture the patient's skin. In such cases, a separate tool may be used to create an incision at the patient's skin first, as discussed.

In some embodiments, after the catheter 61*a* is placed inside the patient, the sheath 62*a* may be advanced distally over the catheter 61*a*. Alternatively, both the catheter 61*a* and the sheath 62*a* may be advanced simultaneously to enter into the patient.

Once the catheter 61*a* and the sheath 62*a* are inserted into the patient, they can be driven to advance through the vasculature of the patient. At sections of the vessel 2000 that are relatively straight, both the catheter 61*a* and the sheath 62*a* may be driven so that they move as one unit. Occasionally, the catheter 61*a* and/or the sheath 62*a* may reach a section of the vessel 2000 that has a bend (e.g., a sharp bend). In such cases, the catheter 61*a* and the sheath 62*a* may be driven in a telescopic manner to advance past the bend.

Figure 23A:
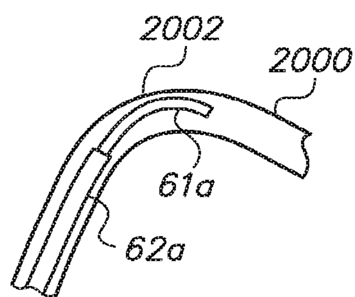
FIG. 23A-23F illustrates a method of using a robotic system to treat tissue in accordance with some embodiments.
Figure 23B:
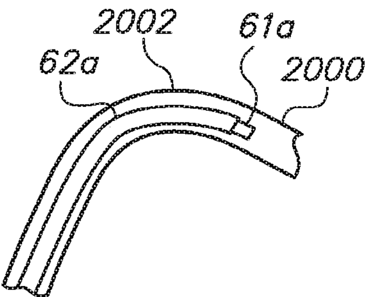
Figure 23C:
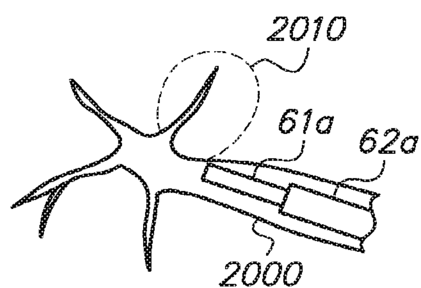

FIGS. 23A-23B illustrate such telescopic technique for advancing the sheath 62*a* and the catheter 61*a* over a bend 2002 along a length of the vessel 2000. In this technique, the catheter 61*a* is positioned with its distal articulation section traversing the bend 2002 and it is locked in this position (FIG. 23A). Next, the sheath 62*a* is advanced over the catheter 61*a* (FIG. 23B), and the catheter 61*a* acts as a rail held in a fixed shape for the sheath 62*a* to glide over. As the sheath 62*a* is advanced further, sections with higher bending stiffness on the sheath 62*a* will pass over the articulated section of the catheter 61*a*, putting an increase load on the catheter 61*a*. The increase in load on the catheter 61*a* may tend to straighten the catheter 61*a*. In some embodiments, the drive assembly of the robotic system 10 maintains the bent shape of the catheter 61*a* by tightening the control wire(s), which has the effect of stiffening the catheter 61*a*. In some embodiments, the robotic system 10 is configured to detect the increased load on the control wires (due to the placement of the sheath 62*a* over the catheter 61*a*) to be detected. The operator, or the robotic system 10, can then apply an equal counteracting load on all the control wires of the catheter 61*a* to ensure that its bent shape is maintained while the sheath 62*a* is advanced over the bend. In other embodiments, the sheath 62*a* may be extremely flexible so that it does not put any significant load on the catheter 61*a* as the sheath 62*a* is advanced over the catheter 61*a*, and/or distort the anatomy.

Figure 23D:
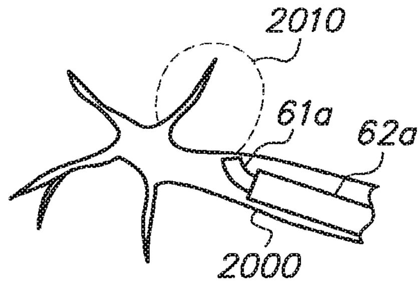

Once the distal end of the catheter 61*a* reaches the target location (FIG. 23C), the distal end of the catheter 61*a* may be steered to create a bend so that the distal opening at the catheter 61*a* faces towards a tissue 2010 that is desired to be treated (FIG. 23D). The steering of the distal end of the catheter 61*a* may be accomplished by receiving a user input at the workstation 2, which generates a user signal in response to the user input. The user signal is transmitted to the controller, which then generates a control signal in response to the user signal. The control signal causes the drive assembly to apply tension to one or more wires inside the catheter 61*a* to thereby bend the distal end of the catheter 61*a* at the desired direction.

Figure 23E:
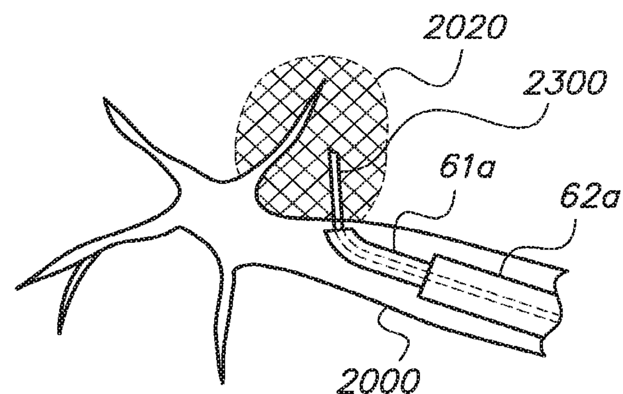

Next, the distal end 2300 of the elongate member 26 is deployed out of the lumen of the catheter 61*a* by advancing the elongate member 26 distally (FIG. 23E). This may be accomplished robotically using the manipulator 24, and/or manually. The sharp distal tip of the elongate member 26 allows the distal end 2300 to penetrate into the target tissue 2010. Also, the flexible section 320 of the elongate member 26 allows the elongate member 26 to follow the curvature of the catheter 61*a* as the elongate member 26 is advanced out of the lumen of the catheter 61*a*. In some embodiments, the distal advancement of the elongate member 26 may be accomplished by receiving a user input at the workstation 2, which generates a user signal in response to the user input. The user signal is transmitted to the controller, which then generates a control signal in response to the user signal. The control signal causes the elongate member manipulator 24 to turn its roller(s) to thereby advance the elongate member 26 distally.

After the distal end 2300 of the elongate member 26 is desirably positioned, the RF generator 350 is then activated to cause the distal end 2300 to deliver RF ablation energy to treat the target tissue 2010. In some embodiments, if the system 10 includes the return electrode 352 that is placed on the patient's skin, the system 10 then delivers the energy in a monopolar configuration. In other embodiments, if the elongate member 26 includes the two electrodes 370*a*, 370*b*, the system 10 may then deliver the energy in a bipolar configuration. The energy is delivered to the target tissue 2010 for a certain duration until a lesion 2020 is created at the target site (FIG. 23E).

In some embodiments, while energy is being delivered by the elongate member 26, cooling fluid may be delivered to the target site through the lumen in the elongate member 26, and out of the distal port 310 and/or side port(s) 312 at the elongate member 26. The cooling fluid allows energy to be delivered to the target tissue in a desired manner so that a lesion 3020 of certain desired size may be created. In other embodiments, the delivery of cooling fluid is optional, and the method does not include the act of delivering cooling fluid.

Figure 23F:
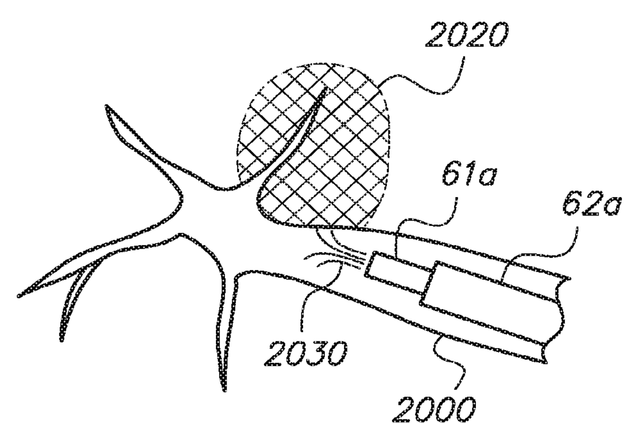

After the lesion 3020 has been created, the elongate member 26 may be removed from the catheter 61*a*, and a substance 2030 may then be delivered to the target site through the lumen of the catheter 61*a* (FIG. 23F). In some embodiments, the removal of the elongate member 26 from the catheter 61*a* may be accomplished by receiving a user input at the workstation 2, which generates a user signal in response to the user input. The user signal is transmitted to the controller, which then generates a control signal in response to the user signal. The control signal causes the elongate member manipulator 24 to turn its roller(s) to thereby retract the elongate member 26 proximally until the entire elongate member 26 is out of the lumen of the catheter 61*a*.

In some embodiments, the substance 2030 may be an embolic material for blocking supply of blood to the target site. In other embodiments, the substance 2030 may be a drug, such as a chemotherapy drug, for further treating tissue at the target site. In further embodiments, the substance 2030 may be one or more radioactive seeds for further treating tissue at the target site through radiation emitted from the radioactive seed(s). In other embodiments, the delivery of the substance 2030 may be optional, and the method may not include the act of delivering the substance 2030.

In some embodiments, if there is another target tissue (e.g., tumor) that needs to be treated, any or all of the above actions may be repeated. For example, in some embodiments, after the first tumor has been ablated, the distal end of the catheter 61*a* may be steered to point to another direction, and the elongate member 26 may be deployed out of the catheter 61*a* again to ablate the second tumor. Also, in other embodiments, the catheter 61*a* may be moved distally or retracted proximally along the length of the vessel 2000 to reach different target sites.

In other embodiments, instead of the telescopic configuration, the robotic system 10 may be configured to drive the catheter 61*a* and the sheath 62*a* in other configurations. For example, in some embodiments, the sheath 62*a* may be bent and acts as guide for directing the catheter 61*a* to move in a certain direction. In such cases, the robotic system 10 may be configured to relax the wires in the catheter 61*a* so that the catheter 61*a* is flexible as it is advanced distally inside the lumen of the sheath 62*a*. Also, in other embodiments, the sheath 62*a* may not be involved in the method. In such cases, the robotic system 10 may be configured to drive the catheter 61*a* without the sheath 62*a* to advance the catheter 61*a* through the vasculature of the patient.

Also, in other embodiments, a guidewire may be used in combination with the catheter 61*a* and/or the sheath 62*a* for advancement of the catheter 61*a* and/or the sheath 62*a* inside the vessel of the patient. In such cases, the elongate member 26 is not inserted into the catheter 61*a*. Instead, the guidewire is coupled to the elongate member manipulator 24, and the guidewire is placed inside the lumen of the catheter 61*a*. The manipulator 24 may then be used to drive the guidewire to advance and/or retract the guidewire. In some cases, the robotic system 10 may advance the guidewire, the catheter 61*a*, and the sheath 62*a* in a telescopic configuration, as similarly discussed.

If a guidewire is initially used to access the interior of the patient, the guidewire may be later exchanged for the elongate member 26. For example, in some embodiments, the guidewire may be exchanged for the elongate member 26 after initial access of the main hepatic artery (or vein). After the distal end of the catheter 61*a* reaches the target site, the guidewire may then be removed from the lumen of the catheter 61*a*, and decoupled from the elongate member manipulator 24. The proximal end of the elongate member 26 is coupled to the elongate member manipulator 24, and the elongate member 26 is then inserted into the lumen of the catheter 61*a*. The elongate member manipulator 24 is then used to drive the elongate member 26 distally until the distal end 2300 of the elongate member 26 exits out of the distal end of the catheter 61*a*, as similarly discussed.

In further embodiments, the elongate member 26 may not be needed to treat tissue. For example, in other embodiments, after the distal end of the catheter 61*a* is desirably placed at a target site, the catheter 61*a* may then be used to deliver a substance (e.g., an agent, a drug, radioactive seed(s), embolic material, etc.) to treat tissue at the target site without ablating the tissue. In some embodiments, the catheter 61*a* itself may be directly used to deliver the substance. In other embodiments, another delivery device (e.g., a tube) may be placed inside the lumen of the catheter 61*a*, and the delivery device is then used to deliver the substance. In such cases, the catheter 61*a* is used indirectly for the delivery of the substance.

In some embodiments, during the treatment method, a localization technique may be employed to determine a location of the instrument inside the patient's body. The term "localization" is used in the art in reference to systems for determining and/or monitoring the position of objects, such as medical instruments, in a reference coordinate system. In one embodiment, the instrument localization software is a proprietary module packaged with an off-the-shelf or custom instrument position tracking system, which may be capable of providing not only real-time or near real-time positional information, such as X-Y-Z coordinates in a Cartesian coordinate system, but also orientation information relative to a given coordinate axis or system. For example, such systems can employ an electromagnetic based system (e.g., using electromagnetic coils inside a device or catheter body). Other systems utilize potential difference or voltage, as measured between a conductive sensor located on the pertinent instrument and conductive portions of sets of patches placed against the skin, to determine position and/or orientation. In another similar embodiment, one or more conductive rings may be electronically connected to a potential-difference-based localization/orientation system, along with multiple sets, preferably three sets, of conductive skin patches, to provide localization and/or orientation data. Additionally, "Fiberoptic Bragg grating" ("FBG") sensors may be used to not only determine position and orientation data but also shape data along the entire length of a catheter or shapeable instrument. In other embodiments, imaging techniques may be employed to determine a location of the instrument inside the patient's body. For examples, x-ray, ultrasound, computed tomography, MRI, etc., may be used in some embodiments.

In other embodiments not comprising a localization system to determine the position of various components, kinematic and/or geometric relationships between various components of the system may be utilized to predict the position of one component relative to the position of another. Some embodiments may utilize both localization data and kinematic and/or geometric relationships to determine the positions of various components. The use of localization and shape technology is disclosed in detail in U.S. patent application Ser. Nos. 11/690,116, now abandoned, 11/176,598, now abandoned, 12/012,795, now abandoned, 12/106,254, issued as U.S. Pat. No. 8,050,523 on Nov. 1, 2011, 12/507,727, now abandoned, 12/822,876, issued as U.S. Pat. No. 8,460,236 on Jun. 11, 2013, 12/823,012, now abandoned, and 12/823,032, issued as U.S. Pat. No. 8,672,837 on Mar. 18, 2014, the entirety of all of which is incorporated by reference herein for all purposes.

Also, in one or more embodiments described herein, the system may further include a sterile barrier positioned between the drive assembly and the elongate member holder, wherein the drive assembly is configured to transfer rotational motion, rotational motion, or both, across the sterile barrier to the rotary members to generate the corresponding linear motion of the elongate member along the longitudinal axis of the elongate member, rotational motion of the elongate member about the longitudinal axis, or both linear motion and rotational motion.

As illustrated in the above embodiments, the robotic technique and system 10 for treating liver tissue is advantageous because it allows the ablation device to reach certain part(s) of the liver through the vessel that may otherwise not be possible to reach using conventional rigid ablation probe. For example, in some embodiments, using the robotic system 10 and the above technique may allow the distal end of the elongate member 26 to reach the lobus quatratus or the lobus spigelii of the liver, which may not be possible to reach by conventional ablation probe. Also, using the elongate member manipulator 24 to position the elongate member 26 is advantageous because it allows accurate positioning of the distal end 2300 of the elongate member 26.

V. Other Clinical Applications

The different driving modes and/or different combinations of driving modes are advantageous because they allow an elongate instrument (catheter 61*a*, sheath 61*b*, elongate member 26, or any combination thereof) to access any part of the vasculature. Thus, embodiments of the system described herein may have a wide variety of applications. In some embodiments, embodiments of the system described herein may be used to treat thoracic aneurysm, thoracoabdominal aortic aneurysm, abdominal aortic aneurysm, isolated common iliac aneurysm, visceral arteries aneurysm, or other types of aneurysms. In other embodiments, embodiments of the system described herein may be used to get across any occlusion inside a patient's body. In other embodiments, embodiments of the system described herein may be used to perform contralateral gait cannulation, fenestrated endograft cannulation (e.g., cannulation of an aortic branch), cannulation of internal iliac arteries, cannulation of superior mesenteric artery (SMA), cannulation of celiac, and cannulation of any vessel (artery or vein). In further embodiments, embodiments of the system described herein may be used to perform carotid artery stenting, wherein the tubular member may be controlled to navigate the aortic arch, which may involve complex arch anatomy. In still further embodiments, embodiments of the system described herein may be used to navigate complex iliac bifurcations.

In addition, in some embodiments, embodiments of the system described herein may be used to deliver a wide variety of devices within a patient's body, including but not limited to: stent (e.g., placing a stent in any part of a vasculature, such as the renal artery), balloon, vaso-occlusive coils, any device that may be delivered over a wire, an ultrasound device (e.g., for imaging and/or treatment), a laser, any energy delivery devices (e.g., RF electrode(s)), etc. In other embodiments, embodiments of the system described herein may be used to deliver any substance into a patient's body, including but not limited to contrast (e.g., for viewing under fluoroscope), drug, medication, blood, etc. In one implementation, after the catheter 61_a_ (leader) is placed at a desired position inside the patient, the catheter 61_a_ and the elongate member 26 may be removed, leaving the sheath 61_b_ to provide a conduit for delivery of any device or substance. In another implementation, the elongate member 26 may be removed, leaving the catheter 61_a_ to provide a conduit for delivery of any device or substance. In further embodiments, the elongate member 26 itself may be used to deliver any device or sub stance.

In further embodiments, embodiments of the system described herein may be used to access renal artery for treating hypertension, to treat uterine artery fibroids, atherosclerosis, and any peripheral artery disease. Also, in other embodiments, embodiments of the system described herein may be used to access the heart. In some embodiments, embodiments of the system may also be used to deliver drug or gene therapy.

In still further embodiments, embodiments of the system described herein may be used to access any internal region of a patient that is not considered a part of the vasculature. For example, in some cases, embodiments of the system described herein may be used to access any part of a digestive system, including but not limited to the esophagus, liver, stomach, colon, urinary tract, etc. In other embodiments, embodiments of the system described herein may be used to access any part of a respiratory system, including but not limited to the bronchus, the lung, etc.

In some embodiments, embodiments of the system described herein may be used to treat a leg that is not getting enough blood. In such cases, the tubular member may access the femoral artery percutaneously, and is steered to the aorta iliac bifurcation, and to the left iliac. Alternatively, the tubular member may be used to access the right iliac. In one implementation, to access the right iliac, the drive assembly may be mounted to the opposite side of the bed (i.e., opposite from the side where the drive assembly is mounted in FIG. 1). In other embodiments, instead of accessing the inside of the patient through the leg, the system may access the inside of the patient through the arm (e.g., for accessing the heart).

In any of the clinical applications mentioned herein, the telescopic configuration of the catheter 61_a_ and the sheath 61_b_ (and optionally the elongate member 26) may be used to get past any curved passage way in the body. For example, in any of the clinical applications mentioned above, a guidewire placed inside the catheter 61_a_ may be advanced first, and then followed by the catheter 61_a_, and then the sheath 61_b_, in order to advance the catheter 61_a_ and the sheath 61_b_ distally past a curved (e.g., a tight curved) passage way. Once a target location is reached, the guidewire may be removed from the catheter 61_a_, and the elongate member 26 may optionally be inserted into the lumen of the catheter 61_a_. The elongate member 26 is then advanced distally until its distal exits from the distal opening at the catheter 61_a_. In other embodiments, the catheter 61_a_ may be advanced first, and then followed by the sheath 61_b_, in order to advance the catheter 61_a_ and the sheath 61_b_ distally past a curved (e.g., a tight curved) passage way. In still further embodiments, the guidewire may be advanced first, and then followed by the catheter 61_a_ the sheath 61_b_ (i.e., simultaneously), in order to advance the catheter 61_a_ and the sheath 61_b_ distally past a curved (e.g., a tight curved) passage way.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present application. Also, any of the features described herein with reference to a robotic system is not limited to being implemented in a robotic system, and may be implemented in any non-robotic system, such as a device operated manually.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed. Also, any optional feature described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that described herein (in which case what is present herein shall prevail). The referenced items are provided solely for their disclosure prior to the filing date of the present application. Nothing herein is to be construed as an admission that any claimed invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art in the field of this application.

Although particular embodiments have been shown and described, it will be understood that they are not intended to limit the claimed inventions, and it will be obvious to those skilled in the art having the benefit of this disclosure that various changes and modifications may be made. The specification and drawings are, accordingly, to be regarded in an illustrative rather than restrictive sense. The claimed inventions are intended to cover alternatives, modifications, and equivalents.

What is claimed is:

1. A sterile adaptor system for a medical robotic system, the sterile adaptor system comprising:

a base having a first opening extending through it, the base being coupleable to an instrument driver and comprising an annular protrusion extending upward from a top surface of the base and positioned to circumferentially surround the first opening;

a cover coupled to the base and coupleable to a splayer, the cover having a second opening extending through it, the second opening being axially aligned with the first opening;

a flexible sheet extending outward from the base to create a sterile barrier over the instrument driver; and a rotary member coupled directly to both the base and the cover, wherein the base and the cover are configured to house the rotary member, wherein the rotary member comprises:

a shaft body having a first end extending downward through the first opening and a second end extending upward through the second opening;

an annular flange extending radially outward from a location of the shaft body between the first and second ends, the annular flange positioned between the base and the cover; and an annular partition extending downward from the flange and forming a circumferential wall around a portion of the shaft body, wherein the annular protrusion of the base and the annular partition of the rotary member cooperate to hold the shaft body within the first opening in a position spaced away from a wall of the base that forms the first opening, to restrict the shaft body from touching the wall of the base.

2. The sterile adaptor system of claim 1, wherein the rotary member is free to rotate about the shaft body of the rotary member.

3. The sterile adaptor system of claim 1, wherein one or more additional first openings extend through the base, wherein one or more additional second openings extend through the cover in positions axially aligned with respective first openings, and wherein the sterile adaptor system further comprises one or more additional rotary members extending through respective additional first and second openings.

4. The sterile adaptor system of claim 1, wherein the sterile adaptor system comprises four rotary members.

5. The sterile adaptor system of claim 1, further comprising the instrument driver.

6. The sterile adaptor system of claim 5, wherein the instrument driver is configured to actuate the rotary member when the first end of the rotary member extends into the instrument driver.

7. The sterile adaptor system of claim 5, wherein the instrument driver is configured to actuate the rotary member in response to a command signal received from a user interface.

8. The sterile adaptor system of claim 5, wherein the instrument driver comprises:

an actuatable member for actuating the rotary member; and a force sensor for sensing an amount of force applied to the actuatable member.

9. The sterile adaptor system of claim 5, wherein the instrument driver comprises a sleeve engage able with the first end of the shaft body.

10. The sterile adaptor system of claim 1, wherein the first end of the rotary member is detachably coupleable to the instrument driver and the second end of the rotary member is detachably coupleable to a splayer rotary member in the splayer.

11. The sterile adaptor system of claim 10, wherein the second end of the rotary member comprises a slot or protrusion for mating with a corresponding feature in the splayer rotary member.

12. The sterile adaptor system of claim 10, wherein, when the rotary member of the sterile adaptor is coupled to the splayer rotary member, the instrument driver is configured to actuate the rotary member in response to a command signal received from a user interface to thereby rotate the splayer rotary member.

13. The sterile adaptor system of claim 10, wherein the first end of the rotary member comprises a slot or protrusion for mating with an actuatable member of the instrument driver.

14. The sterile adaptor system of claim 1, wherein the instrument driver and the splayer comprise mating features configured to mate with splines on the shaft body.

15. The sterile adaptor system of claim 1, wherein the base further comprises a second annular protrusion circumferentially disposed around the first opening and extending upward, and wherein the flange of the rotary member further comprises a second annular partition extending downward.

16. The sterile adaptor system of claim 1, further comprising the splayer, wherein the splayer comprises:

a splayer rotary member;

an elongate member having a distal end, a proximal end, and a lumen extending between the distal and proximal ends; and a control wire having a distal end coupled to the distal end of the elongate member, and a proximal end coupled to the splayer rotary member such that actuation of the splayer rotary member actuates the control wire and thereby manipulates the distal end of the elongate member.

17. The sterile adapter system of claim 1, wherein the base is configured to couple to a guide mounting plate.

* * * * *